US009353190B2

(12) United States Patent
Rubenstein et al.

(10) Patent No.: US 9,353,190 B2
(45) Date of Patent: May 31, 2016

(54) COMPOSITIONS, SYSTEMS AND METHODS FOR THE DIAGNOSIS, PREVENTION AND TREATMENT OF DISORDERS ASSOCIATED WITH AZETIDINE-2-CARBOXYLIC ACID

(71) Applicant: The Board of Trustees of the Leland Stanford Junior University, Palo Alto, CA (US)

(72) Inventors: Edward Rubenstein, Hillsborough, CA (US); Kevin Grimes, Mountain View, CA (US)

(73) Assignee: The Board of Trustees of the Leland Stanford Junio CA (US)

( * ) Notice: Subject to any disclaimer, the term of this patent is extended or adjusted under 35 U.S.C. 154(b) by 0 days.

(21) Appl. No.: 14/139,233

(22) Filed: Dec. 23, 2013

(65) Prior Publication Data

US 2014/0113836 A1 Apr. 24, 2014

Related U.S. Application Data

(60) Continuation-in-part of application No. 12/943,441, filed on Nov. 10, 2010, now Pat. No. 8,617,624, which is a division of application No. 11/693,423, filed on Mar. 29, 2007, now Pat. No. 7,915,380.

(60) Provisional application No. 60/791,269, filed on Apr. 12, 2006, provisional application No. 60/787,267, filed on Mar. 30, 2006.

(51) Int. Cl.
*A61K 38/45* (2006.01)
*C07K 16/44* (2006.01)
*C07K 14/00* (2006.01)
*G01N 33/68* (2006.01)
*A23L 1/305* (2006.01)

(52) U.S. Cl.
CPC ............... *C07K 16/44* (2013.01); *A23L 1/3053* (2013.01); *A61K 38/45* (2013.01); *C07K 14/001* (2013.01); *C12Y 203/01* (2013.01); *G01N 33/6896* (2013.01); *G01N 2800/285* (2013.01)

(58) Field of Classification Search
CPC ...................................................... A21D 8/042
See application file for complete search history.

(56) References Cited

U.S. PATENT DOCUMENTS 3,785,063 A 1/1974 Bishop
3,862,337 A 1/1975 Osborne

OTHER PUBLICATIONS

Rubenstein, J Neuropathol Exp Neurol V67 No. 11, Nov. 2008 pp. 1035-1040.*

Animal Feed Resources Information System, Mung bean (*Vigna radiata*) (pp. 1-10. Feedipedia—Animal Feed Resources Information System—INRA CIRAD AFZ and FAO © 2012 Last updated on Oct. 24, 2012 00:44:38).

Fowden (Amino Acids of Polygonatum, 1958, pp. 626-629).

Rubenstein, E. [2000] Biologic Effects of and clinical disorders caused by nonprotein amino acids. Medicine, 79:80-89.

Fowden L. & Richmond M.H. [1963] Replacement of proline by azetidine-w-carboxylic acid during biosynthesis of protein. Biochm. Biophys. Acta 71:450-61.

Trotter E.W. et al. [2002] Misfolded proteins are competent to mediate a subset of the responses to heat shock in *Saccharomyces cerevisiae*. J. Bioi. Chern. 277:44817-44825.

Muramatsu T. et al. [1992]1nduction of the 72-kD heat shock protein in organ-cultured normal human skin. J. Invest. Dermatol. 98:786-790.

Ohtsuka K. et al. [1990] A novel40-kDa protein induced by heat shock and other stresses in mammalian and avian cells. Biochem. Biophys. Res. Commun. 166:642-647.

Oikarinen A. et al. [1976] Effect of L-azetidine-2-carboxylic acid on glycosylations of collagen in chick-embryo tendon cells. Biochem. J. 160:639-645.

Majamaa K. [1981] Effect of prevention of procollagen triple-helix formation on proline 3-hydroxylation in freshly isolated chick-embryo tendon cells. Biochem. J. 196:203-206.

Hilfer S.R. & Pakstis G.L. [1977]1nterference with thyroid histogenesis by inhibitors of collagen synthesis. J. Cell Bioi. 75:446-463.

Bradamante Z. & Hall B.K. [1980] The role of epithelial collagen and proteoglycan in the initiation of osteogenesis by avian neural crest cells. Anat. Rec. 197:305-315.

Hall B.K. [1978] Use of the L-proline analog, L-azetidine-2-carboxylic acid (LACA) to analyse embryonic growth and determination and expression of the chondrogenic phenotype in vivo and in vitro. Anat. Rec. 190:243-256.

Barber M. et al. [1979]Synthesis and biological activities of [7-(azetidine-2-carboxylic acid)]-oxytocin and -lysine-vasopressin. Int. J. Pept. Protein Res. 14:247-261.

Baum B.J. et al. [1975]1ncorporation of L-azetidine-2-carboxylic acid into hemoglobin in rabbit reticulocytes in vitro. J. Biol. Chern. 250:1464-1471.

Cho M.-1., & Garant P.R. [1985] Effects of L-azetidine-2-carboxylic acid on matrix secretion and golgi structure in fibroblasts and osteoblasts of the mouse.Anat. Rec. 212:232-238.

Tan E.M.L. et al. [1983] Proline analogues inhibit human skin fibroblast growth and collagen production in culture. J. Invest. Dermatol. 80:261-267.

Dunn M.A. et al. [1977] Liver collagen synthesis in murine schistosomiasis. J. Clin. Invest. 59:666-674.

(Continued)

*Primary Examiner* — Karlheinz R Skowronek
*Assistant Examiner* — Li Lee
(74) *Attorney, Agent, or Firm* — Thomas|Horstemeyer, LLP

(57) ABSTRACT

The present disclosure provides synthesized peptides containing azetidine-2-carboxylic acid (Aze), methods for detecting antibodies to peptides containing Aze, and methods for diagnosing conditions associated with misincorporation of Aze into host proteins.

11 Claims, 8 Drawing Sheets

(56) References Cited

OTHER PUBLICATIONS

Alescio, T. [1973] Effect of a proline analogue, azetidine-2-carboxylic acid, on the morphogenesis in vitro of mouse embryonic lung. J. Embryol. Exp. Morphol. 29:439-451.

Rocha V. et al. [1986] Basal lamina inhibition suppresses synthesis of calcium-dependent proteins associated with mammary epithelial cell spreading. Exp. Cell Res. 165:450-460.

Tsai F.-H. et al. [1990] Synthesis and peptide bond orientation in tetrapeptides containing L-azetidine-2-carboxylic acid and L-proline. Biopolymers 30:1039-1049.

Alvarez, 0. M., Mertz, P.M., & Eaglstein, W. H. (1982). The effect of the proline analogue 1-azetidine-2-carboxylic acid (LACA) on epidermal and dermal wound repair. Plastic and reconstructive surgery, 69(2), 284.

Adamson, I. Y., & King, G. M. (1987). L-azetidine-2-carboxylic acid retards lung growth and surfactant synthesis in fetal rats. Laboratory investigation; a journal of technical methods and pathology, 57(4), 439-445.

Van De Water, T. R., & Galinovic-Schwartz, V. (1986). Dysmorphogenesis of the inner ear: disruption of extracellular matrix (ECM) formation by an L-proline analog in otic explants. J. Craniofac. Genet. Dev. Bioi, 6, 113-129.

Nomura, M., Nakamori, S., & Takagi, H. (2003). Characterization of novel acetyltransferases found in budding and fission yeasts that detoxify a proline analogue, azetidine-2-carboxylic acid. Journal of biochemistry, 133(1), 67-74.

Rubenstein et al. (2006) Azetidine-2-carboxylic acid in garden beets (*Beta vulgaris*). Phytochemistry 67 898-903. Available online Mar. 3, 2006.

Fowden (1972) Amino Acid Complement of Plants. Photochemistry. 1972; 11 (7):2271-2276.

Bell, EA (2003) Nonprotein Amino Acids of Plants: Significance in Medicine, Nutrition, and Agriculture. J. Agric. Food Chem. 51,2854-2865.

Srivastava et al. (2012) Potassium Channel KIR4.1 as an Immune Target in Multiple Sclerosis, N Engl J Med. 367:115-123.

* cited by examiner proline azetidine-2-carboxylic acid

SEQUENCE LISTING

```
<160> NUMBER OF SEQ ID NOS: 18

<210> SEQ ID NO 1
<211> LENGTH: 9
<212> TYPE: PRT
<213> ORGANISM: Homo sapiens

<400> SEQUENCE: 1

Thr Pro Arg Thr Pro Pro Pro Ser Gln
1               5


<210> SEQ ID NO 2
<211> LENGTH: 9
<212> TYPE: PRT
<213> ORGANISM: Artificial sequence
<220> FEATURE:
<223> OTHER INFORMATION: Chemically synthesized Aze-substituted fragment
      of myelin basic protein
<220> FEATURE:
<221> NAME/KEY: MISC_FEATURE
<222> LOCATION: (2)..(2)
<223> OTHER INFORMATION: Xaa = azetedine-2-carboxylic acid (Aze)

<400> SEQUENCE: 2
```

-continued

Thr Xaa Arg Thr Pro Pro Pro Ser Gln
1 5

<210> SEQ ID NO 3
<211> LENGTH: 9
<212> TYPE: PRT
<213> ORGANISM: Artificial Sequence
<220> FEATURE:
<223> OTHER INFORMATION: Chemically synthesized Aze-substituted fragment of myelin basic protein
<220> FEATURE:
<221> NAME/KEY: MISC_FEATURE
<222> LOCATION: (5)..(5)
<223> OTHER INFORMATION: Xaa = azetedine-2-carboxylic acid (Aze)
<220> FEATURE:
<221> NAME/KEY: MISC_FEATURE
<222> LOCATION: (6)..(6)
<223> OTHER INFORMATION: Xaa = azetedine-2-carboxylic acid (Aze)
<220> FEATURE:
<221> NAME/KEY: MISC_FEATURE
<222> LOCATION: (7)..(7)
<223> OTHER INFORMATION: Xaa = azetedine-2-carboxylic acid (Aze)

<400> SEQUENCE: 3

Thr Pro Arg Thr Xaa Xaa Xaa Ser Gln
1 5

<210> SEQ ID NO 4
<211> LENGTH: 9
<212> TYPE: PRT
<213> ORGANISM: Artificial Sequence
<220> FEATURE:
<223> OTHER INFORMATION: Chemically synthesized Aze-substituted fragment of myelin basic protein
<220> FEATURE:
<221> NAME/KEY: MISC_FEATURE
<222> LOCATION: (2)..(2)
<223> OTHER INFORMATION: Xaa = azetedine-2-carboxylic acid (Aze)
<220> FEATURE:
<221> NAME/KEY: MISC_FEATURE
<222> LOCATION: (5)..(5)
<223> OTHER INFORMATION: Xaa = azetedine-2-carboxylic acid (Aze)

<400> SEQUENCE: 4

Thr Xaa Arg Thr Xaa Pro Pro Ser Gln
1 5

<210> SEQ ID NO 5
<211> LENGTH: 9
<212> TYPE: PRT
<213> ORGANISM: Artificial Sequence
<220> FEATURE:
<223> OTHER INFORMATION: Chemically synthesized Aze-substituted fragment of myelin basic protein
<220> FEATURE:
<221> NAME/KEY: MISC_FEATURE
<222> LOCATION: (2)..(2)
<223> OTHER INFORMATION: Xaa = azetedine-2-carboxylic acid (Aze)
<220> FEATURE:
<221> NAME/KEY: MISC_FEATURE
<222> LOCATION: (5)..(5)
<223> OTHER INFORMATION: Xaa = azetedine-2-carboxylic acid (Aze)
<220> FEATURE:
<221> NAME/KEY: MISC_FEATURE
<222> LOCATION: (6)..(6)
<223> OTHER INFORMATION: Xaa = azetedine-2-carboxylic acid (Aze)

<400> SEQUENCE: 5

Thr Xaa Arg Thr Xaa Xaa Pro Ser Gln
1 5

-continued

<210> SEQ ID NO 6
<211> LENGTH: 9
<212> TYPE: PRT
<213> ORGANISM: Artificial Sequence
<220> FEATURE:
<223> OTHER INFORMATION: Chemically synthesized Aze-substituted fragment of myelin basic protein
<220> FEATURE:
<221> NAME/KEY: MISC_FEATURE
<222> LOCATION: (2)..(2)
<223> OTHER INFORMATION: Xaa = azetedine-2-carboxylic acid (Aze)
<220> FEATURE:
<221> NAME/KEY: MISC_FEATURE
<222> LOCATION: (5)..(5)
<223> OTHER INFORMATION: Xaa = azetedine-2-carboxylic acid (Aze)
<220> FEATURE:
<221> NAME/KEY: MISC_FEATURE
<222> LOCATION: (6)..(6)
<223> OTHER INFORMATION: Xaa = azetedine-2-carboxylic acid (Aze)
<220> FEATURE:
<221> NAME/KEY: MISC_FEATURE
<222> LOCATION: (7)..(7)
<223> OTHER INFORMATION: Xaa = azetedine-2-carboxylic acid (Aze)

<400> SEQUENCE: 6

Thr Xaa Arg Thr Xaa Xaa Xaa Ser Gln
1 5

<210> SEQ ID NO 7
<211> LENGTH: 9
<212> TYPE: PRT
<213> ORGANISM: Artificial Sequence
<220> FEATURE:
<223> OTHER INFORMATION: Chemically synthesized Aze-substituted fragment of myelin basic protein
<220> FEATURE:
<221> NAME/KEY: MISC_FEATURE
<222> LOCATION: (5)..(5)
<223> OTHER INFORMATION: Xaa = azetedine-2-carboxylic acid (Aze)
<220> FEATURE:
<221> NAME/KEY: MISC_FEATURE
<222> LOCATION: (6)..(6)
<223> OTHER INFORMATION: Xaa = azetedine-2-carboxylic acid (Aze)

<400> SEQUENCE: 7

Thr Pro Arg Thr Xaa Xaa Pro Ser Gln
1 5

<210> SEQ ID NO 8
<211> LENGTH: 9
<212> TYPE: PRT
<213> ORGANISM: Artificial Sequence
<220> FEATURE:
<223> OTHER INFORMATION: Chemically synthesized Aze-substituted fragment of myelin basic protein
<220> FEATURE:
<221> NAME/KEY: MISC_FEATURE
<222> LOCATION: (5)..(5)
<223> OTHER INFORMATION: Xaa = azetedine-2-carboxylic acid (Aze)

<400> SEQUENCE: 8

Thr Pro Arg Thr Xaa Pro Pro Ser Gln
1 5

<210> SEQ ID NO 9
<211> LENGTH: 24
<212> TYPE: PRT
<213> ORGANISM: Homo sapiens

<400> SEQUENCE: 9

Asp Glu Asn Pro Val Val His Phe Phe Lys Asn Ile Val Thr Pro Arg
1 5 10 15

-continued

```
Thr Pro Pro Pro Ser Gln Gly Lys
            20


<210> SEQ ID NO 10
<211> LENGTH: 24
<212> TYPE: PRT
<213> ORGANISM: Artificial Sequence
<220> FEATURE:
<223> OTHER INFORMATION: Chemically synthesized Aze-substituted fragment
      of myelin basic protein
<220> FEATURE:
<221> NAME/KEY: MISC_FEATURE
<222> LOCATION: (4)..(4)
<223> OTHER INFORMATION: Xaa = azetedine-2-carboxylic acid (Aze)

<400> SEQUENCE: 10

Asp Glu Asn Xaa Val Val His Phe Phe Lys Asn Ile Val Thr Pro Arg
1               5                   10                  15

Thr Pro Pro Pro Ser Gln Gly Lys
            20


<210> SEQ ID NO 11
<211> LENGTH: 24
<212> TYPE: PRT
<213> ORGANISM: Artificial Sequence
<220> FEATURE:
<223> OTHER INFORMATION: Chemically synthesized Aze-substituted fragment
      of myelin basic protein
<220> FEATURE:
<221> NAME/KEY: MISC_FEATURE
<222> LOCATION: (15)..(15)
<223> OTHER INFORMATION: Xaa = azetedine-2-carboxylic acid (Aze)

<400> SEQUENCE: 11

Asp Glu Asn Pro Val Val His Phe Phe Lys Asn Ile Val Thr Xaa Arg
1               5                   10                  15

Thr Pro Pro Pro Ser Gln Gly Lys
            20


<210> SEQ ID NO 12
<211> LENGTH: 24
<212> TYPE: PRT
<213> ORGANISM: Artificial Sequence
<220> FEATURE:
<223> OTHER INFORMATION: Chemically synthesized Aze-substituted fragment
      of myelin basic protein
<220> FEATURE:
<221> NAME/KEY: MISC_FEATURE
<222> LOCATION: (18)..(18)
<223> OTHER INFORMATION: Xaa = azetedine-2-carboxylic acid (Aze)

<400> SEQUENCE: 12

Asp Glu Asn Pro Val Val His Phe Phe Lys Asn Ile Val Thr Pro Arg
1               5                   10                  15

Thr Xaa Pro Pro Ser Gln Gly Lys
            20


<210> SEQ ID NO 13
<211> LENGTH: 24
<212> TYPE: PRT
<213> ORGANISM: Artificial Sequence
<220> FEATURE:
<223> OTHER INFORMATION: Chemically synthesized Aze-substituted fragment
      of myelin basic protein
<220> FEATURE:
<221> NAME/KEY: MISC_FEATURE
<222> LOCATION: (19)..(19)
<223> OTHER INFORMATION: Xaa = azetedine-2-carboxylic acid (Aze)
```

-continued

<400> SEQUENCE: 13

Asp Glu Asn Pro Val Val His Phe Phe Lys Asn Ile Val Thr Pro Arg
1 5 10 15

Thr Pro Xaa Pro Ser Gln Gly Lys
20

<210> SEQ ID NO 14
<211> LENGTH: 24
<212> TYPE: PRT
<213> ORGANISM: Artificial Sequence
<220> FEATURE:
<223> OTHER INFORMATION: Chemically synthesized Aze-substituted fragment of myelin basic protein
<220> FEATURE:
<221> NAME/KEY: MISC_FEATURE
<222> LOCATION: (20)..(20)
<223> OTHER INFORMATION: Xaa = azetedine-2-carboxylic acid (Aze)

<400> SEQUENCE: 14

Asp Glu Asn Pro Val Val His Phe Phe Lys Asn Ile Val Thr Pro Arg
1 5 10 15

Thr Pro Pro Xaa Ser Gln Gly Lys
20

<210> SEQ ID NO 15
<211> LENGTH: 38
<212> TYPE: PRT
<213> ORGANISM: Homo sapiens

<400> SEQUENCE: 15

Gly Val Val Trp Tyr Leu Val Ala Val Ala His Gly Asp Leu Leu Glu
1 5 10 15

Leu Asp Pro Pro Ala Asn His Thr Pro Cys Val Val Gln Val His Thr
20 25 30

Leu Thr Gly Ala Phe Leu
35

<210> SEQ ID NO 16
<211> LENGTH: 38
<212> TYPE: PRT
<213> ORGANISM: Artificial Sequence
<220> FEATURE:
<223> OTHER INFORMATION: Chemically synthesized Aze-substituted fragment of potassium channel KIR4.1 protein
<220> FEATURE:
<221> NAME/KEY: MISC_FEATURE
<222> LOCATION: (19)..(19)
<223> OTHER INFORMATION: Xaa = azetedine-2-carboxylic acid (Aze)

<400> SEQUENCE: 16

Gly Val Val Trp Tyr Leu Val Ala Val Ala His Gly Asp Leu Leu Glu
1 5 10 15

Leu Asp Xaa Pro Ala Asn His Thr Pro Cys Val Val Gln Val His Thr
20 25 30

Leu Thr Gly Ala Phe Leu
35

<210> SEQ ID NO 17
<211> LENGTH: 38
<212> TYPE: PRT
<213> ORGANISM: Artificial Sequence
<220> FEATURE:
<223> OTHER INFORMATION: Chemically synthesized Aze-substituted fragment of potassium channel KIR4.1 protein -continued

```
<220> FEATURE:
<221> NAME/KEY: MISC_FEATURE
<222> LOCATION: (20)..(20)
<223> OTHER INFORMATION: Xaa = azetedine-2-carboxylic acid (Aze)

<400> SEQUENCE: 17

Gly Val Val Trp Tyr Leu Val Ala Val Ala His Gly Asp Leu Leu Glu
1               5                   10                  15

Leu Asp Pro Xaa Ala Asn His Thr Pro Cys Val Val Gln Val His Thr
            20                  25                  30

Leu Thr Gly Ala Phe Leu
        35


<210> SEQ ID NO 18
<211> LENGTH: 38
<212> TYPE: PRT
<213> ORGANISM: Artificial Sequence
<220> FEATURE:
<223> OTHER INFORMATION: Chemically synthesized Aze-substituted fragment
      of potassium channel KIR4.1 protein
<220> FEATURE:
<221> NAME/KEY: MISC_FEATURE
<222> LOCATION: (25)..(25)
<223> OTHER INFORMATION: Xaa = azetedine-2-carboxylic acid (Aze)

<400> SEQUENCE: 18

Gly Val Val Trp Tyr Leu Val Ala Val Ala His Gly Asp Leu Leu Glu
1               5                   10                  15

Leu Asp Pro Pro Ala Asn His Thr Xaa Cys Val Val Gln Val His Thr
            20                  25                  30

Leu Thr Gly Ala Phe Leu
        35
```

COMPOSITIONS, SYSTEMS AND METHODS FOR THE DIAGNOSIS, PREVENTION AND TREATMENT OF DISORDERS ASSOCIATED WITH AZETIDINE-2-CARBOXYLIC ACID

CROSS-REFERENCE TO RELATED APPLICATION

This application is a continuation-in-part application of copending US application entitled "Compositions, Systems and Methods for the Diagnosis, Prevention and Treatment of Disorders Associated with Azetidine-2-Carboxylic Acid", Ser. No. 12/943,441, filed Nov. 10, 2010, which is a divisional of U.S. patent application entitled "Compositions, Systems and Methods for the Diagnosis, Prevention and Treatment of Disorders Associated with Azetidine-2-Carboxylic Acid" U.S. Pat. No. 7,915,380, filed Mar. 29, 2007 and issued Mar. 29, 2011, which claimed priority to and the benefit of copending U.S. provisional patent application entitled "Methods for the Diagnosis, Prevention and Treatment of Disorders Associated with Azetidine-2-Carboxylic Acid", Ser. No. 60/787,267, filed Mar. 30, 2006 and U.S. provisional patent application of the same title having Ser. No. 60/791,269, filed Apr. 12, 2006, both of which are incorporated herein by reference in their entirety.

SEQUENCE LISTING

The present disclosure includes a sequence listing incorporated herein by reference in its entirety.

FIELD OF THE INVENTION(S)

The present disclosure relates to the diagnosis, prevention, and treatment of diseases associated with and/or caused by exposure to or ingestion of the nonprotein amino acid azetidine-2-carboxylic acid.

BACKGROUND

Although bacteria, plants and animals construct their proteins from the same set of 20 amino acids (22, including selenocysteine and pyrrolysine), there are in nature a large number of other amino acids that are not incorporated into peptides or proteins. Such compounds, for which there are no codons, are referred to as nonprotein amino acids.

Many of these compounds serve as sentries that protect vital plant structures by poisoning predators. Plants that tend to harbor nonprotein amino acids include the Fabaceae (e.g., legumes, beans, peas, peanuts, soy, clover, some trees), the Curcurbitaceae (e.g., gourds, pumpkins, cucumbers), as well as fruits (e.g., apple, banana, cherry, cranberry, date, pear) and nuts (e.g., almond, pine nut, walnut), and Chenopodiaceae (e.g., beets). The consumption of most of these foods/plants in usual amounts causes no apparent harm to humans; however, the ingestion of some nonprotein amino acids leads to a variety of disease states, some of which can be lethal.

Azetidine-2-carboxylic acid (Aze) is a plant nonprotein amino acid identical to proline except that the ring of Aze has four members and the ring of proline has five, as illustrated in FIG. 1 showing proline (left) and Aze (right). The tRNAs of numerous species do not discriminate between Aze and proline, and, therefore, Aze is misincorporated in place of proline into proteins, including those of humans. Such misassembly can result in disorders owing to protein malformation, dysfunction, and immunogenicity. In addition, in various studies Aze administration has resulted in a wide range of teratogenic effects in chicks, ducks, hamsters, mice, and rabbits.

Since Aze was not believed to be a constituent of the human diet, its role in the pathogenesis of disease in humans has remained unexplored. However, Aze has shown to be present in sugar beets and in table beets (*Beta vulgaris*). Sugar beet agriculture, especially in the Northern Hemisphere, has become widespread during the past 150 years, and now accounts for nearly 30 percent of the world's supply of sucrose. Sugar beet byproducts are used as a dietary supplement for some livestock, therefore opening a channel for the possible entry of Aze into the human food chain.

The intrusion of Aze into the food chain would have significant implications regarding disease in humans. The misincorporation of Aze in place of proline may be especially pathogenic when the malformed protein is involved in critical functions such as DNA repair or embryogenesis. Proteins in which there are silent genetic mutations may become disease-producing should acquired misassembly owing to Aze substitution for proline also occur. Furthermore, long-lived proteins, such as collagen and myelin basic protein, may become sinks into which endogenously re-circulating Aze, as well as exogenous dietary Aze, eventually accumulate.

Therefore, if Aze is, in fact, entering the human food chain, there is a critical need for methods and systems for detecting Aze in both human and animal foodstuffs as well as methods and systems for treating food consumable by humans and animals to remove or otherwise inactivate Aze. What is further needed are methods and systems for detecting Aze in human proteins, diagnosing disorders associated with Aze, and treating disorders associated with Aze.

SUMMARY

Briefly described, the present disclosure provides methods and systems for preventing, detecting, diagnosing, and treating conditions associated with misincorporation of Aze into host proteins. In embodiments, the present disclosure provides synthesized peptides containing azetidine-2-carboxylic acid (Aze), methods for detecting antibodies to peptides containing Aze, and methods for diagnosing conditions associated with misincorporation of Aze into host proteins.

Embodiments of the present disclosure further include synthesized polypeptides including a sequence selected from SEQ ID NOs: 10, 11, 12, 13, 14, 16, 17, and 18 as well as antibodies capable of binding a polypeptide having a sequence selected from: SEQ ID NOs: 10, 11, 12, 13, 14, 16, 17, and 18.

Also provided are methods of detecting antibodies to Aze in a host including the following steps: providing at least one test peptide including Aze, where the test peptide is a derivative of a wild-type peptide, the test peptide having at least one proline residue replaced by Aze; providing a sample from a host, where the sample includes host antibodies; contacting the host sample with the at least one test peptide; and detecting binding between the peptide and an antibody from the host sample, where binding indicates the presence in the host sample of an antibody to the Aze-containing peptide.

Additional embodiments of methods of detecting antibodies to Aze include: providing a library of test peptides having Aze in place of at least one proline residue; contacting the library of peptides with a composition including antibodies; and detecting binding between the peptides and an antibody from the antibody composition, where binding indicates the presence of an antibody to the Aze-containing peptide. In an exemplary embodiment the library of peptides includes at least one of the peptides of SEQ ID NOs: 10, 11, 12, 13, 14, 16, 17, and 18. In embodiments, the library of peptides includes one or more test peptides having an amino acid sequence corresponding to a portion of a wild-type sequence of one or more of the following human proteins: myelin basic protein, potassium channel Kir4.1, collagen, hypoxia-inducible factor, profilins, ion channel proteins, vesicular glutamate transporters, and hemoglobins, where the wild-type sequence of each protein portion has at least one proline residue, and where at least one such proline of each corresponding test peptide in the library has been replaced by Aze.

The details of some exemplary embodiments of the methods, compositions, features, and systems of the present disclosure are set forth in the description below. Other features, objects, and advantages of the disclosure will be apparent to one of skill in the art upon examination of the following description, drawings, examples and claims. It is intended that all such additional systems, methods, compositions, features, and advantages be included within this description, be within the scope of the present disclosure, and be protected by the accompanying claims.

BRIEF DESCRIPTION OF THE DRAWINGS

The disclosure can be better understood with reference to the following drawings. The components in the drawings are not necessarily to scale, emphasis instead being placed upon clearly illustrating the principles of the present disclosure. The drawings are described in greater detail in the description and examples below.

DETAILED DESCRIPTION

Figure 1:
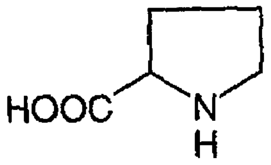
FIG. 1 illustrates the chemical structure of proline (left) and azetidine-2-carboxylic acid (Aze) (right).
Figure 1:
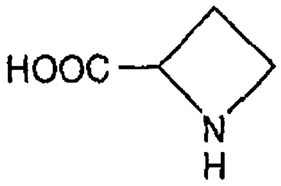

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

The following examples are put forth so as to provide those of ordinary skill in the art with a complete disclosure and description of how to perform the methods and use the compositions and compounds disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

Embodiments of the present disclosure will employ, unless otherwise indicated, techniques of medicine, pharmacology, biochemistry, molecular biology, genetics, and the like, which are within the skill of the art. Such techniques are explained fully in the literature.

It must be noted that, as used in the specification and the appended claims, the singular forms “a,” “an,” and “the” include plural referents unless the context clearly dictates otherwise. Thus, for example, reference to “a support” includes a plurality of supports. In this specification and in the claims that follow, reference will be made to a number of terms that shall be defined to have the following meanings unless a contrary intention is apparent.

Prior to describing the various embodiments, the following definitions are provided and should be used unless otherwise indicated.

DEFINITIONS

The terms "native," "wild type", or "unmodified" polypeptide, protein or enzyme, are used herein to provide a reference point for the polypeptide, protein, or enzyme prior to any modification, mutation, and the like, as described herein. Typically, the unmodified, native, or wild type polypeptide, protein, or enzyme has an amino acid sequence that corresponds substantially to the amino acid sequence of the polypeptide, protein, or enzyme as it generally occurs in nature and/or in vivo.

As used herein, the term "comprising" is intended to mean that the compositions and methods include the recited elements, but not excluding others. "Consisting essentially of," when used to define compositions and methods, shall mean excluding other elements of any essential significance to the combination, and for peptides shall mean excluding amino acids that would change the function of the peptide or otherwise interfere with its intended purpose. Thus, a composition consisting essentially of the elements as defined herein would not exclude trace contaminants from the isolation and purification method and pharmaceutically acceptable carriers, such as phosphate buffered saline, preservatives, and the like. Similarly, a peptide sequence consisting essentially of a specified amino acid sequence would not exclude additional amino acids on either end of the sequence that do not interfere with the intended purpose/function of the peptide sequence. "Consisting of" shall mean excluding more than trace elements of other ingredients (for compositions), additional amino acids (for peptide sequences), and substantial method steps for administering the compositions of this disclosure. Embodiments defined by each of these transition terms are within the scope of this disclosure.

The term "residue" as used herein refers to an amino acid that is incorporated into a peptide. The amino acid may be a naturally occurring amino acid and, unless otherwise limited, may encompass known analogs of natural amino acids that can function in a similar manner as naturally occurring amino acids.

As used herein, "polynucleotides" include single or multiple stranded configurations, where one or more of the strands may or may not be completely aligned with another. The terms "polynucleotide" and "oligonucleotide" shall be generic to polydeoxynucleotides (containing 2-deoxy-D-ribose), to polyribonucleotides (containing D-ribose), to any other type of polynucleotide which is an N-glycoside of a purine or pyrimidine base, and to other polymers in which the conventional backbone has been replaced with a non-naturally occurring or synthetic backbone or in which one or more of the conventional bases has been replaced with a non-naturally occurring or synthetic base. An "oligonucleotide" generally refers to a nucleotide multimer of about 2 to 100 nucleotides in length, while a "polynucleotide" includes a nucleotide multimer having any number of nucleotides greater than 1, although they are often used interchangeably.

It will be appreciated that, as used herein, the terms "nucleoside" and "nucleotide" will include those moieties which contain not only the naturally occurring purine and pyrimidine bases, e.g., adenine (A), thymine (T), cytosine (C), guanine (G), or uracil (U), but also modified purine and pyrimidine bases and other heterocyclic bases which have been modified (these moieties are sometimes referred to herein, collectively, as "purine and pyrimidine bases and analogs thereof"). Such modifications include, e.g., diaminopurine and its derivatives, inosine and its derivatives, alkylated purines or pyrimidines, acylated purines or pyrimidines, thiolated purines or pyrimidines, and the like, or the addition of a protecting group such as acetyl, difluoroacetyl, trifluoroacetyl, isobutyryl, benzoyl, 9-fluorenylmethoxycarbonyl, phenoxyacetyl, dimethylformamidine, N,N-diphenyl carbamate, or the like. The purine or pyrimidine base may also be an analog of the foregoing; suitable analogs will be known to those skilled in the art and are described in the pertinent texts and literature. Common analogs include, but are not limited to, 1-methyladenine, 2-methyladenine, N6-methyladenine, N6-isopentyladenine, 2-methylthio-N6-isopentyladenine, N,N-dimethyladenine, 8-bromoadenine, 2-thiocytosine, 3-methylcytosine, 5-methylcytosine, 5-ethylcytosine, 4-acetylcytosine, 1-methylguanine, 2-methylguanine, 7-methylguanine, 2,2-dimethylguanine, 8-bromoguanine, 8-chloroguanine, 8-aminoguanine, 8-methylguanine, 8-thioguanine, 5-fluorouracil, 5-bromouracil, 5-chlorouracil, 5-iodouracil, 5-ethyluracil, 5-propyluracil, 5-methoxyuracil, 5-hydroxymethyluracil, 5-(carboxyhydroxymethyl)uracil, 5-(methylaminomethyl)uracil, 5-(carboxymethylaminomethyl)-uracil, 2-thiouracil, 5-methyl-2-thiouracil, 5-(2-bromovinyl)uracil, uracil-5-oxyacetic acid, uracil-5-oxyacetic acid methyl ester, pseudouracil, 1-methylpseudouracil, queosine, inosine, 1-methylinosine, hypoxanthine, xanthine, 2-aminopurine, 6-hydroxyaminopurine, 6-thiopurine, and 2,6-diaminopurine.

The term "polypeptides" and "protein" include proteins and fragments thereof. Polypeptides are disclosed herein as amino acid residue sequences. Those sequences are written left to right in the direction from the amino to the carboxy terminus. In accordance with standard nomenclature, amino acid residue sequences are denominated by either a three letter or a single letter code as indicated as follows: Alanine (Ala, A), Arginine (Arg, R), Asparagine (Asn, N), Aspartic Acid (Asp, D), Cysteine (Cys, C), Glutamine (Gln, Q), Glutamic Acid (Glu, E), Glycine (Gly, G), Histidine (H is, H), Isoleucine (Ile, I), Leucine (Leu, L), Lysine (Lys, K), Methionine (Met, M), Phenylalanine (Phe, F), Proline (Pro, P), Serine (Ser, S), Threonine (Thr, T), Tryptophan (Trp, W), Tyrosine (Tyr, Y), and Valine (Val, V).

"Variant" refers to a polypeptide that differs from a reference polypeptide, but retains essential properties. A typical variant of a polypeptide differs in amino acid sequence from another, reference polypeptide. Generally, differences are limited so that the sequences of the reference polypeptide and the variant are closely similar overall and, in many regions, identical. A variant and reference polypeptide may differ in amino acid sequence by one or more modifications (e.g., substitutions, additions, and/or deletions). A substituted or inserted amino acid residue may or may not be one encoded by the genetic code. A variant of a polypeptide may be naturally occurring such as an allelic variant, or it may be a variant that is not known to occur naturally.

Modifications and changes can be made in the structure of the polypeptides of the present disclosure and still obtain a molecule having similar characteristics as the polypeptide (e.g., a conservative amino acid substitution). For example, certain amino acids can be substituted for other amino acids in a sequence without appreciable loss of activity. Because it is the interactive capacity and nature of a polypeptide that defines that polypeptide's biological functional activity, certain amino acid sequence substitutions can be made in a polypeptide sequence and nevertheless obtain a polypeptide with like properties.

In making such changes, the hydropathic index of amino acids can be considered. The importance of the hydropathic amino acid index in conferring interactive biologic function on a polypeptide is generally understood in the art. It is known that certain amino acids can be substituted for other amino acids having a similar hydropathic index or score and still result in a polypeptide with similar biological activity. Each amino acid has been assigned a hydropathic index on the basis of its hydrophobicity and charge characteristics. Those indices are: isoleucine (+4.5); valine (+4.2); leucine (+3.8); phenylalanine (+2.8); cysteine/cysteine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is believed that the relative hydropathic character of the amino acid determines the secondary structure of the resultant polypeptide, which in turn defines the interaction of the polypeptide with other molecules, such as enzymes, substrates, receptors, antibodies, antigens, and the like. It is known in the art that an amino acid can be substituted by another amino acid having a similar hydropathic index and still obtain a functionally equivalent polypeptide. In such changes, the substitution of amino acids whose hydropathic indices are within ±2 is preferred, those within ±1 are particularly preferred, and those within ±0.5 are even more particularly preferred.

Substitution of like amino acids can also be made on the basis of hydrophilicity, particularly, where the biological functional equivalent polypeptide or peptide thereby created is intended for use in immunological embodiments. The following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); proline (−0.5±1); threonine (−0.4); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). It is understood that an amino acid can be substituted for another having a similar hydrophilicity value and still obtain a biologically equivalent, and in particular, an immunologically equivalent polypeptide. In such changes, the substitution of amino acids whose hydrophilicity values are within ±2 is preferred, those within ±1 are particularly preferred, and those within ±0.5 are even more particularly preferred.

As outlined above, amino acid substitutions are generally based on the relative similarity of the amino acid side-chain substituents, for example, their hydrophobicity, hydrophilicity, charge, size, and the like. Exemplary substitutions that take various of the foregoing characteristics into consideration are well known to those of skill in the art and include (original residue: exemplary substitution): (Ala: Gly, Ser), (Arg: Lys), (Asn: Gln, His), (Asp: Glu, Cys, Ser), (Gln: Asn), (Glu: Asp), (Gly: Ala), (His: Asn, Gln), (Ile: Leu, Val), (Leu: Ile, Val), (Lys: Arg), (Met: Leu, Tyr), (Ser: Thr), (Thr: Ser), (Tip: Tyr), (Tyr: Trp, Phe), and (Val: Ile, Leu). Embodiments of this disclosure thus contemplate functional or biological equivalents of a polypeptide as set forth above. In particular, embodiments of the polypeptides can include variants having about 50%, 60%, 70%, 80%, 90%, and 95% sequence identity to the polypeptide of interest.

As used herein "functional variant" refers to a variant of a protein or polypeptide that can perform the same functions or activities as the original protein or polypeptide, although not necessarily at the same level (e.g., the variant may have enhanced, reduced or changed functionality, so long as it retains the basic function).

"Identity," as known in the art, is a relationship between two or more polypeptide sequences, as determined by comparing the sequences. In the art, "identity" also refers to the degree of sequence relatedness between polypeptide as determined by the match between strings of such sequences. "Identity" and "similarity" can be readily calculated by known methods, including, but not limited to, those described in the following references: Computational Molecular Biology, Lesk, A. M., Ed., Oxford University Press, New York, 1988; Biocomputing: Informatics and Genome Projects, Smith, D. W., Ed., Academic Press, New York, 1993; Computer Analysis of Sequence Data, Part I, Griffin, A. M., and Griffin, H. G., Eds., Humana Press, New Jersey, 1994; Sequence Analysis in Molecular Biology, von Heinje, G., Academic Press, 1987; and Sequence Analysis Primer, Gribskov, M. and Devereux, J., Eds., M Stockton Press, New York, 1991; and Carillo, H., and Lipman, D., SIAM J Applied Math., 48: 1073 (1988).

Preferred methods to determine identity are designed to give the largest match between the sequences tested. Methods to determine identity and similarity are codified in publicly available computer programs. The percent identity between two sequences can be determined by using analysis software (e.g., Sequence Analysis Software Package of the Genetics Computer Group, Madison Wis.) that incorporates the Needelman and Wunsch, (J. Mol. Biol., 48: 443-453, 1970) algorithm (e.g., N BLAST, and XBLAST). The default parameters are used to determine the identity for the polypeptides of the present disclosure.

By way of example, a polypeptide sequence may be identical to the reference sequence, that is be 100% identical, or it may include up to a certain integer number of amino acid alterations as compared to the reference sequence such that the % identity is less than 100%. Such alterations are selected from: at least one amino acid deletion, substitution, including conservative and non-conservative substitution, or insertion, and wherein said alterations may occur at the amino- or carboxy-terminal positions of the reference polypeptide sequence or anywhere between those terminal positions, interspersed either individually among the amino acids in the reference sequence or in one or more contiguous groups within the reference sequence. The number of amino acid alterations for a given % identity is determined by multiplying the total number of amino acids in the reference polypeptide by the numerical percent of the respective percent identity (divided by 100) and then subtracting that product from said total number of amino acids in the reference polypeptide.

The term "isolated" means separated from constituents, cellular and otherwise, in which the polynucleotide, peptide, polypeptide, protein, antibody, or fragments thereof, are normally associated with in nature. In one aspect of this disclosure, an isolated polynucleotide is separated from the 3' and 5' contiguous nucleotides with which it is normally associated with in its native or natural environment, e.g., on the chromosome. As is apparent to those of skill in the art, a non-naturally occurring polynucleotide, peptide, polypeptide, protein, antibody, or fragments thereof, does not require "isolation" to distinguish it from its naturally occurring counterpart. In addition, a "concentrated," "separated" or "diluted" polynucleotide, peptide, polypeptide, protein, antibody, or fragments thereof, is distinguishable from its naturally occurring counterpart in that the concentration or number of molecules per volume is greater than "concentrated" or less than "separated" than that of its naturally occurring counterpart. A polynucleotide, peptide, polypeptide, protein, antibody, or fragments thereof, which differs from the naturally occurring counterpart in its primary sequence or for example, by its glycosylation pattern, need not be present in its isolated form since it is distinguishable from its naturally occurring counterpart by its primary sequence, or alternatively, by another characteristic such as glycosylation pattern.

Although not explicitly stated for each of the embodiments disclosed herein, it is to be understood that all of the above embodiments for each of the compositions disclosed below and under the appropriate conditions, are provided by this disclosure. Thus, a non-naturally occurring polynucleotide is provided as a separate embodiment from the isolated naturally occurring polynucleotide. A protein produced in a bacterial cell is provided as a separate embodiment from the naturally occurring protein isolated from a eukaryotic cell in which it is produced in nature. Thus, as used herein, the term "isolated peptide" refers to a naturally-occurring peptide separated from constituents, cellular and otherwise, in which the polynucleotide, peptide, polypeptide, protein, antibody, or fragments thereof, are normally associated with in nature The term "synthesized peptide" as used herein refers to a peptide that is synthesized by human action, such as, but not limited to, peptides synthesized by de novo by chemical synthesis techniques and peptides synthesized by genetically manipulated bacterial cells by methods known to those of skill in the art.

An "enzyme," as used herein, is a polypeptide that acts as a catalyst, which facilitates and generally speeds the rate at which chemical reactions proceed but does not alter the direction or nature of the reaction.

As used herein, the term "promoter" includes all sequences capable of driving transcription of a coding sequence. In particular, the term "promoter" as used herein refers to a DNA sequence generally described as the 5' region of a gene, located proximal to the start codon. The transcription of an adjacent gene(s) is initiated at the promoter region. The term "promoter" also includes fragments of a promoter that are functional in initiating transcription of the gene.

A "primer" as used herein generally refers to a nucleic acid strand, or a related molecule, that serves as a starting point for replication, and is used in amplification techniques, such as the polymerase chain reaction (PCR). Primers used in such techniques are usually relatively short (generally about 20-50 base pairs), artificially synthesized polynucleotide strands. In PCR, primers are used to select the polynucleotide sequence to be amplified by the PCR process.

The term "expression" as used herein describes the process undergone by a structural gene to produce a polypeptide. It is a combination of transcription and translation.

The term "plasmid" as used herein refers to a non-chromosomal double-stranded DNA sequence including an intact "replicon" such that the plasmid is replicated in a host cell.

As used herein, the term "vector" or "expression vector" is used in reference to a vehicle used to introduce a nucleic acid sequence into a cell. A vector may include a DNA molecule, linear or circular, which includes a segment encoding a polypeptide of interest operably linked to additional segments that provide for its transcription and translation upon introduction into a host cell or host cell organelles. Such additional segments may include promoter and terminator sequences, and may also include one or more origins of replication, one or more selectable markers, an enhancer, a polyadenylation signal, etc. Expression vectors are generally derived from yeast or bacterial genomic or plasmid DNA, or viral DNA, or may contain elements of both.

The term "transformation" refers to the introduction of DNA or RNA into cells in such a way as to allow gene expression.

The term "coupled" as used herein refers to the binding, bonding, or other forms of association of a protein, specifically the association of a protein having an active site and a substrate or ligand.

As used herein, the term "host" or "organism" includes both humans, mammals (e.g., cats, dogs, horses, etc.), and other living species. In embodiments, hosts/organisms are in need of treatment for conditions/diseases. A living organism can be as simple as, for example, a single eukaryotic cell or as complex as a mammal.

The term "composition" can include one or more chemical compounds.

The term "derivative" refers to a modification to the disclosed compounds including, but not limited to, hydrolysis, reduction, or oxidation products, of the disclosed compounds, as well as mutations to the disclosed polypeptides. Hydrolysis, reduction, and oxidation reactions are known in the art.

The term "functional derivative" refers to a derivative of the disclosed compounds that retains the function of the disclosed compound, although not necessarily at the same level of functionality (e.g., the variant may have enhanced, reduced or changed functionality, so long as it retains the basic function).

The term "therapeutically effective amount" as used herein refers to that amount of the compound being administered which will relieve or prevent to some extent one or more of the symptoms to be treated. In reference to conditions/diseases caused directly or indirectly by exposure to Aze, a therapeutically effective amount refers to that amount which has the effect of preventing the condition/disease from occurring in an animal that may be predisposed to the disease but does not yet experience or exhibit symptoms of the condition/disease (prophylactic treatment), alleviation of symptoms of the condition/disease, diminishment of extent of the condition/disease, stabilization (e.g., not worsening) of the condition/disease, preventing the spread of condition/disease, delaying or slowing of the condition/disease progression, amelioration or palliation of the condition/disease state, and combinations thereof.

"Pharmaceutically acceptable salt" refers to those salts that retain the biological effectiveness and properties of the free bases and which are obtained by reaction with inorganic or organic acids such as, but not limited to, hydrochloric acid, hydrobromic acid, sulfuric acid, nitric acid, phosphoric acid, methanesulfonic acid, ethanesulfonic acid, p-toluenesulfonic acid, salicylic acid, malic acid, maleic acid, succinic acid, tartaric acid, citric acid, and the like.

A "pharmaceutical composition" refers to a mixture of one or more of the compounds described herein, or pharmaceutically acceptable salts thereof, with other chemical components, such as physiologically acceptable carriers and excipients. One purpose of a pharmaceutical composition is to facilitate administration of a compound to an organism.

As used herein, a "pharmaceutically acceptable carrier" refers to a carrier or diluent that does not cause significant irritation to an organism and does not abrogate the biological activity and properties of the administered compound.

An "excipient" refers to an inert substance added to a pharmaceutical composition to further facilitate administration of a compound. Examples of excipients include, but are not limited to, calcium carbonate, calcium phosphate, various sugars and types of starch, cellulose derivatives, gelatin, vegetable oils, and polyethylene glycols.

As used herein, "treat", "treating", and "treatment" are an approach for obtaining beneficial or desired clinical results. For purposes of embodiments of this disclosure, beneficial or desired clinical results include, but are not limited to, preventing the condition/disease from occurring in an animal that may be predisposed to the condition/disease but does not yet experience or exhibit symptoms of the disease (prophylactic treatment), alleviation of symptoms of the condition/disease, diminishment of extent of the condition/disease, stabilization (e.g., not worsening) of the condition/disease, preventing spread of the condition/disease, delaying or slowing of the condition/disease progression, amelioration or palliation of the condition/disease state, and combinations thereof. In addition, "treat", "treating", and "treatment" can also mean prolonging survival as compared to expected survival if not receiving treatment.

As used herein, the term "topically active agents" refers to compositions of the present disclosure that elicit pharmacological responses at the site of application (contact) to a host.

As used herein, the term "topically" refers to application of the compositions of the present disclosure to the surface of the skin and mucosal cells and tissues.

As used herein, the term "inhibit" and/or "reduce" generally refers to the act of reducing, either directly or indirectly, a function, activity, or behavior relative to the natural, expected, or average or relative to current conditions. For instance, something that inhibits or reduces incorporation of Aze into a host protein might interfere with, stop, or slow such incorporation. For instance, if a certain action or composition is said to reduce incorporation of Aze into a host protein, this may indicate reducing such incorporation below what would be expected if the action had not been taken or the composition had not been administered.

As used herein, the term "modulate," "modify," and/or "modulator" generally refers to the act of directly or indirectly promoting/activating or interfering with/inhibiting a specific function or behavior. In some instances a modulator may increase and/or decrease a certain activity or function relative to its natural state or relative to the average level of activity that would generally be expected or relative to a current level of activity.

As used herein, the term "disorder" includes both conditions and diseases of a host (e.g., a human or other mammal). Additionally, a disorder "associated with Aze" or "mediated by Aze" indicates that the disorder is somehow linked with the misincorporation of Aze into host proteins. The misincorporation of Aze into the host proteins may not directly cause the disease or condition, but it may trigger, enhance, or otherwise influence the state, progression, or incidence of the disease or condition. As used herein "misincorporation" of Aze into a host protein refers to the replacement of a proline residue by Aze in a host protein.

As used herein "auto-immune disorder" refers to certain diseases and/or conditions in which a host's immune system attacks the host's own cells and/or tissues. Exemplary autoimmune disorders include multiple sclerosis, lupus, rheumatoid arthritis, and the like.

As used herein, the term "exogenous DNA" or "exogenous nucleic acid sequence" or "exogenous polynucleotide" refers to a nucleic acid sequence that was introduced into a cell or organelle from an external source. Typically the introduced exogenous sequence is a recombinant sequence.

As used herein, the term "transfection" refers to the introduction of a nucleic acid sequence into the interior of a membrane enclosed space of a living cell, including introduction of the nucleic acid sequence into the cytosol of a cell as well as the interior space of a mitochondria, nucleus or chloroplast. The nucleic acid may be in the form of naked DNA or RNA, associated with various proteins or the nucleic acid may be incorporated into a vector or a chromosome. A "transformed" cell is thus a cell transfected with a nucleic acid sequence.

The term "recombinant" generally refers to a non-naturally occurring nucleic acid, nucleic acid construct, or polypeptide. Such non-naturally occurring nucleic acids include combinations of DNA molecules of different origin that are joined using molecular biology technologies, or natural nucleic acids that have been modified, for example that have deletions, substitutions, inversions, insertions, etc. Recombinant also refers to the polypeptide encoded by the recombinant nucleic acid. Non-naturally occurring nucleic acids or polypeptides include nucleic acids and polypeptides modified by man.

As used herein, the term "selectable marker" refers to a gene product that confers a selectable phenotype, such as antibiotic resistance, on a transformed cell or organism (e.g., a plant). Selectable markers are encoded by expressible DNA sequences, which are sometimes referred to herein as "selectable marker genes."

As used herein, the term "promoter" or "promoter region" refers to the 5' regulatory regions of a gene, including promoters per se, as well as other transcriptional and translational regulatory sequences.

The term "operably linked" indicates that the regulatory sequences necessary for expression of the coding sequences are placed in the DNA molecule in the appropriate positions relative to the coding sequence so as to effect expression of the coding sequence. This same definition is sometimes applied to the arrangement of coding sequences and transcription control elements (e.g. promoters, enhancers, and termination elements) in an expression vector. The term "transgene" refers to an artificial gene which is used to transform a cell of an organism, such as a bacterium or a plant.

Having defined some of the terms herein, the various embodiments of the disclosure will be described.

General Discussion:

The ingestion of or exposure to azetidine-2-carboxylic acid (Aze) may result in various conditions and/or diseases in forms, such as, but not limited to: developmental disorders, especially of the central nervous system; congenital malformations; autoimmune disorders, especially those involving long-lasting structural proteins such as collagen and myelin basic protein; disorders of ion channels; disorders of other molecules in which proline plays a critical structural or functional role, such as hypoxia-inducible factor, profilin, and the hinge region of immunoglobulins; and degenerative diseases, again especially those related to defective mechanical properties of collagen and related molecules in bones, joints, tendons, and supportive structures.

Thus, the present disclosure is directed to compositions and methods for treating or preventing conditions associated with exposure to Aze, whether by elimination or reduction of Aze in the environment, testing for the presence of Aze in foodstuff and other materials, amelioration of the effects of Aze, methods to determine susceptibility to Aze related disorders, and/or tools for studying the relation of Aze to various diseases and conditions.

Aspects, compositions, methods, features, and advantages of the present disclosure will be or become apparent to one with skill in the art upon examination of the following drawings and detailed description. It is intended that all such compositions, methods, features, and advantages be included within this description, be within the scope of the present disclosure.

Azetidine-2-carboxylic Acid (Aze)

Fowden demonstrated that azetidine-2-carboxylic acid can be incorporated into proteins in place of proline. (Fowden L., Richmond M. H. [1963] Biochm. Biophys. Acta 71:450-61, which is hereby incorporated by reference herein). In principle, azetidine-2-carboxylic acid can replace proline in any protein, altering its structure, including its folding, or altering its function or creating new epitopes. Thus, the misincorporation of azetidine-2-carboxylic acid results in disease states owing to malformation of, dysfunction of, and expression of novel epitopes on peptides or proteins. Such events occurring during embryogenesis lead to various disorders including congenital malformations. Misincorporation is the result of the inability of some prolyl-tRNA synthetases to discriminate between proline and azetidine-2-carboxylic acid.

Azetidine-2-Carboxylic Acid in Food

Azetidine-2-carboxylic acid was first isolated from Liliaceae by Fowden in 1956, who later confirmed that azetidine-2-carboxylic acid was present in sugar beets. Sugar beets are processed for their high concentration of sucrose, and their by products are used as feed for livestock and other animals. Fodder beets are fed to livestock. The identification of azetidine-2-carboxylic acid as a substantial constituent of the amino acids in garden beets was made by E. Rubenstein, H. Zhou, K. M. Krasinska, A. Chien, and C. H. Becker, (as disclosed in "Azetidine-2-carboxylic acid in garden beets (*Beta vulgaris*)" Phytochemistry, March 2006, which is hereby incorporated by reference).

Garden beets are a popular table food, and are eaten in many regions of the world. The widespread consumption of garden beets elevates them to the status of a staple in a number of heavily populated regions. As already mentioned, sugar beets are not only used for the production of sucrose and certain forms of molasses, but also are an important component of the diet of dairy and meat-producing livestock, including cattle, sheep, and pigs. Thus, to the extent that azetidine-2-carboxylic acid finds its way from beets into the feed of such animals, their milk, their milk products, and their meat serve as secondary sources of azetidine-2-carboxylic acid in the food consumed by humans and other animals. However, to date no studies have investigated the presence of Aze in any such food products. The presence of Aze in milk and baker's yeast is demonstrated in Example 1, below. This shows that Aze is indeed present in the human food chain, which raises critical health concerns and demonstrates a need for food testing systems and procedures for testing food for Aze levels.

Some Teratogenic and Toxic Effects of Azetidine-2-Carboxylic Acid

In laboratory experiments, azetidine-2-carboxylic acid has been shown to interfere with a number of biological processes; however, the pathogenetic role of azetidine-2-carboxylic acid has not been recognized in human or veterinary medicine.

The introduction of azetidine-2-carboxylic acid into a protein in place of proline causes conformational changes. For instance, altered bond angles and have been shown to change the tertiary structure of a collagen strand. Such effects have been identified in various tissues. Exposure to the compound in mice has caused the failure to form normal basal lamina of mammary epithelial cells, suppressing the activity of calcium-binding proteins needed for cell spreading. In the same animal model, the proline analogue disrupts collagen secretion and results in dysgenesis of the embryonal otic elements.

Azetidine-2-carboxylic acid has been responsible for arrested lung growth and impaired secretion of surfactant in embryonic rats and mice. Similarly, hepatic collagen synthesis has been inhibited in murine schistosomiasis. The hair of mice fed azetidine-2-carboxylic acid exhibits abnormal physical properties resulting from alterations of the helical structure of keratin.

Numerous studies have been conducted on skin. Abnormal biochemical, mechanoelastic, and structural changes have been observed in murine dermal collagen I. In human skin, impaired fibroblast growth has been noted, and procollagen has been found in non-triple-helical conformations. In pigs, the nonprotein amino acid has been associated with delayed wound healing. Abnormal development of murine dental structures includes failure of ligamentous growth, abnormalities of fibroblasts and osteoblasts, and delayed morphogenesis.

Azetidine-2-carboxylic acid has replaced proline in human and in rabbit hemoglobin. The nonprotein amino acid has substituted for proline in synthetic peptides such as oxytocin and vasopressin. Abnormal somite mesenchyme differentiation, defective chondrogenesis, impaired bud development, and absent vertebra in chick embryos, along with abnormal development of the avian neural crest leading to failure of osteogenesis of the mandibular process, have implications about the deleterious effects of the compound on early neural differentiation and growth. Abnormal uropygial development in duck embryos has also been observed. Other anatomic abnormalities induced by the nonprotein amino acid in chicks include interference with thyroid histogenesis and failure of differentiation of the testis. Tendon abnormalities such as absence of normal triple helix formation of collagen and increased collagen glycosylation have also been observed in chicks. Azetidine-2-carboxylic acid fed to pregnant mice predisposes to cleft palate. Exposure during pregnancy in hamsters has been reported to result in fetal weight abnormalities, tissue hemorrhages, cleft palate, retarded ossifications, and shortened bones.

Administration of the nonprotein amino acid has induced the formation of novel proteins including heat shock proteins in human and avian tissues. Azetidine-2-carboxylic acid causes misfolding of proteins. The compound has been found to induce the expression of heat shock factor-regulated genes in yeast.

Thus, ingestion of, or other exposure to, azetidine-2-carboxylic acid by humans and other animals can result in abnormal embryogenesis, congenital anomalies, and structural and functional changes in peptides, proteins, cells, tissues, and organs. This raises the need for diagnostic tests and methods for detecting Aze present in host proteins, as well as methods and compositions for reducing the incorporation of ingested Aze into host proteins.

Role of Proline in Proteins and Implications for Disease Pathogenesis

Proline is unlike any of the other 22 protein amino acids in that its amino group is covalently locked within a five-member ring, as shown in FIG. 1. Such bonding constrains the torsion angles of the peptide union between the nitrogen group of a proline and the carboxyl group of the adjacent amino acid. Therefore such bonds impart a rigid flexure at that point in a string of amino acids. In the peptide union between other amino acids, the nitrogen atom of the amino group of one and the hydrogen atom of the carboxyl group of the other occupy opposite positions (trans) in the plane of the peptide bond. Because of the unique electron environment of proline's nitrogen, there is a strong tendency for the hydrogen and oxygen atoms to be on the same side of the plane (cis), a configuration that causes significant changes in bond angles, altering regional conformation. The process of cis-trans isomerization converts minor changes in the electronic milieu into major mechanical events, transduced by proline. Another exceptional property of proline is that its nitrogen is bonded to only one hydrogen atom, and therefore proline cannot function as a hydrogen bond donor, and can serve only as a hydrogen bond acceptor.

These properties account for the special role of proline in molecular structure and function, features that resulted in the evolutionary selection of proline, among hundreds of other naturally occurring amino acids, as one of the set of protein amino acids, distinguished by the existence of a DNA codon that directs their incorporation into proteins.

Because of the bond angle flexures, a proline residue often changes the direction of a chain and results in a turn. Some proline-rich sequences create a characteristic extended helix, which is the configuration a strand in collagen. On the other hand, the intrusion of a proline disrupts the basic architecture of alpha helices or beta sheets. Prolines can serve as the initial amino acid of alpha helices and at the edges of beta sheets.

Due to proline's powerful effects on protein architecture, as described above, the displacement of a proline by a molecular analogue, such as Aze, may result in untoward effects on the conformation, charge distribution and function of a protein. The adverse phenotypic effects of replacing proline with another amino acid are a likely explanation for the fact that such substitution is probably the least frequent type of hereditary point mutation. A compilation of such mutations indicates the replacement of proline by another amino acid accounts for only 224 of a total of 12,648 changed residues in mutation sites.

Transient exposure to Aze, leading to misincorporation into proteins that are turned over rapidly, may not have severe ramifications, unless the molecule is engaged in critical activities such as those involved in embryogenesis and DNA repair. Misincorporation into proteins with long lifetimes can have critical consequences. The degradation of short-lived molecules leads to the endogenous release of the foreign molecules, their recirculation, and successive rounds of misincorporation. Catabolic states are likely to result in increased internal release. This cycle pauses when the nonprotein amino acids become engaged in the synthesis of protein with a long lifetime, where they lurk in residence and are poised to do their damage. Thus, long-lived proteins become a sink into which the foreign molecules accumulate. The gradual accretion of a nonprotein amino acid is likely to have its deleterious effects on durable proteins, typified by collagen and myelin basic protein, molecules that are laid down to a considerable extent during morphogenesis, childhood and adolescence, a time span of apparent health, during which silent events may predestine future disease.

Consumed at critical times during early pregnancy, azetidine-2-carboxylic acid increases the risk of a variety of congenital abnormalities. A small stream of the nonprotein amino acid entering human protein synthesis can result in the gradual accumulation of abnormally formed, dysfunctional, and immunogenic molecules. The consequences can be especially severe in the case of proteins with a long half-life, such as collagen.

Thus, the clinical expression of disease, including autoimmune disorders such as multiple sclerosis, may not be apparent until years or even decades after the ingestion begins. In the case of an autoimmune disorder, after a critical epitopic exposure threshold is reached, the disease phase begins and may simmer or exacerbate periodically thereafter indefinitely. The continued ingestion of small quantities of the pathogenetic agents may result in lifelong illness. (Rubenstein, E. [2000] Medicine, 79:80-89).

Misincorporation can also occur in immuno-proteins and in the soluble and cellular mediators of the immune system. Multiple sclerosis serves as an exemplar of a disorder that can arise as a result of misincorporation of a nonprotein amino acid, such as azetidine-2-carboxylic acid. The disease is a relapsing or chronically recurring demyelinating disorder of the central nervous system. There is strong evidence that both genetic and environmental factors participate in its pathogenesis. (Lindsay and Wolinsky, Demyelinating Diseases, in Scientific American Medicine, Dale and Federman; eds, WebMD Inc., New York, 2003, 11:IX:1-12. Rosati G. [2001] Neurol. Sci. 22:117-139). Therefore, this demonstrates a critical need for methods and systems for determining the role of Aze in human disease, as well as methods and systems for diagnosing and treating such diseases. In particular, there is a need for methods and systems for determining the effect of Aze misincorporation into a host's proteins and polypeptides, and for treating related disorders. The importance of proline in several proteins, and some implications related to its replacement by Aze, are described below.

Possible Effects of Misincorporation of Aze for Proline in Exemplary Proteins

Laboratory data have established the pathogenic potential of Aze displacement of proline in some proteins where proline plays a significant role. A few examples, chosen to illustrate the diverse manifestations of this disease mechanism, include studies involving ion channels, collagen, hemoglobin, and hypoxia-inducible factor.

a. Ion Channels:

In neurotransmitter gated ion channels of the Cys-loop receptor superfamily, a proline residue in the apex of the loop between two transmembrane helices links receptor binding to the gating of the channel through a cis-trans isomerization. Thus, this proline serves as swivel point that exerts a nozzle-like action on the opening and closing of the channel pore.

Substituting Aze for proline in this position has been shown to impair channel function. (Lummis et al., Cis-trans isomerization at a proline opens the pore of a neuro-transmitter-gated ion channel. Nature, 2005, 438: 248-52). Fluctuating blood levels of Aze, arising from exogenous intake or endogenous release, may play a role in precipitating sporadic episodes of intermittent disorders that may be caused by dysfunction of ion channels, such as epilepsy, myopathies, migraine, and arrhythmias.

b. Collagens:

The collagens are long, thin molecules comprised of three helical chains which wrap around each other in a braided fashion. They are the most abundant protein of mammals, and may account for as much as 30% of the proteins in a human body. There are distinctive types of collagen in various tissues, such as bone, cartilage, skin, blood vessels, and the viscera. Proline constitutes about 15 percent of the amino acid residues. The prolyls become hydroxylated at the C-4 position in nascent collagen strands in a reaction catalyzed by prolyl hydroxylase. Steric repulsion between the bulky rings of proline and hydroxyproline, which are on the outside of the molecule, stabilizes the triple helix structure. There are no hydrogen bonds within a strand, but the strands are hydrogen bonded to each other.

Because of the abundance of prolyls in collagen and their critical role in its conformation, collagen molecules are highly vulnerable to the effects of the misincorporation of Aze. This is especially true during the time span of embryonic biosynthesis and growth into adulthood. Numerous studies have demonstrated that Aze exposure causes severe impairment of collagen formation in chicks, mice, pigs, and humans. (Rubenstein, Biologic effects and clinical disorders caused by nonprotein amino acids. Medicine, 2000, 79:80-89). Just as many proline residues in newly synthesized collagen become hydroxylated to form hydroxyproline, Aze hydroxylation has been identified in epi-hydroxymugineic acid, suggesting that such hydroxylation of Aze may occur within misassembled collagen as well. (von Wirén et al., Hydroxylated phytosiderophore species possess an enhanced chelatestability and affinity for iron (III), Plant Physiol., 2000 124:1149-57). Due to the widespread use of collagen in the body and the abundance of proline in collagen, misincorporation of Aze into collagen could lead to a wide variety of disorders.

c. Hemoglobins:

Aze has been shown to be misincorporated into human hemoglobin in place of proline. (Rubenstein, 2000). There are at least ten well-defined hemoglobinopathies associated with proline mutations. (OMIM, Number 63903, Johns Hopkins University, Baltimore, Md., Jun. 20, 2006). Some have deleterious effects on gas exchange, and some of these hemoglobins are unstable and associated with severe hemolytic disease. In addition, the misincorporation of Aze in place of proline in other hemoglobinopathies may contribute to clinical exacerbations. The factors that trigger such events are often difficult to identify.

d. Hypoxia Inducible Transcription Factors

Many of the sub-molecular details of an oxygen-sensing and hypoxia-correcting complex cellular mechanism in organisms ranging from nematodes to man have recently been elucidated. Prolyl residues play a critical role in the regulation of the HIF mechanism. (Schofield and Ratcliffe, Oxygen sensing by HIF hydroxylases. Nat. Rev. Mol. Cell. Biol. 2004, 5: 343-54).

An entire repertoire of interacting molecules is involved in the tightly coordinated activities of the HIF mechanism. These can be assigned to three general functions: hypoxia sensing, upregulation of hypoxia-correcting DNA coding sequences, and the prompt proteolytic destruction of the key components of the system after local hypoxia has been ameliorated.

HIF is a heterodimer comprised of two basic subunits, each a helix-loop-helix protein, referred to as HIF$\alpha$ and HIF$\beta$. The dimer binds to DNA protein coding regions and upregulates the transcription of 40 or more proteins that correct the effects of local hypoxia. These products subserve three categories of response: increased production of vascular endothelial growth factor, increased production of erythropoietin, and increased production of the cascade of enzymes involved in glycolysis. HIF$\alpha$ exists in three forms. HIF 1$\alpha$ and HIF 2$\alpha$ are closely related and are rapidly induced by hypoxia; HIF 3$\alpha$ displays structural differences and its regulation is unclear. HIF$\beta$ is a constitutively produced nuclear transcription protein.

HIF 1$\alpha$ and HIF 2$\alpha$ contain two independently functioning oxygen-dependent degradation domains as well as two transactivation regions. HIF 1$\alpha$ subunits are highly inducible by hypoxia. Both HIF 1$\alpha$ and HIF 2$\alpha$ are proteolyzed within two separate oxygen-dependent degradation domains, sequences located in the central region of the molecule. HIF 1$\alpha$ and HIF 1$\beta$ also encompass two transactivation regions, whose function and inactivation are incompletely understood. HIF 1$\alpha$ appears to be inactivated by an independent mechanism that excludes it from the nucleus in the presence of oxygen. HIF$\alpha$ subunits contain sequences that respond to hypoxia, to cobaltous ions, and to iron chelators. Each of the three HIF$\alpha$ regions that respond to hypoxia do so as a result of oxygen-dependent enzymatic hydroxylation of specific proline residues.

Three 2-oxoglutarate-dependent oxygenases with the capacity to catalyze HIF-prolyl hydroxylation have been identified. They have an absolute requirement for molecular oxygen as a co-substrate and therefore provide a direct link between oxygen availability and the regulation of HIF. The prolyl 4-hydroxylases regulate the HIFs by hydroxylating a Leu-Xaa-Xaa-Leu-Ala-Pro motif (SEQ. ID. NO. 9). Substitution of the proline by azetidine-2-carboxylic acid or by 3,4 dehydroproline, but not any other residue, leads to a high rate of uncoupled 2-oxoglutarate decarboxylation with no hydroxylation.

Hydroxylation of prolyl residues regulates interactions with the von Hippel-Lindau suppressor (pVHL), the component of the ubiquitin-ligase complex that designates HIF$\alpha$ subunits for proteosomal destruction. Hydroxylation increases the affinity of HIF$\alpha$ peptides for the pVHL-elongin B-elongin C (VBC) complex by a thousand-fold. The critical difference between the hydroxylated and non-hydroxylated residues is the formation of two hydrogen bonds between the alcohol of the hydroxylated prolines and two residues of pVHL. Under hypoxic conditions, prolyl hydroxylation is suppressed, and therefore the HIF$\alpha$ subunit escapes pVHL-mediated destruction and promptly accumulates to high levels.

Genetic abnormalities of the von Hippel-Lindau tumor suppressor—elongin proteins have been associated with benign and malignant neoplasms including renal cell carcinoma, pheochromocytoma, pancreatic tumors, and retinal, cerebellar, and spinal hemangioblastomas. (OMIM Number 193300, Johns Hopkins University, Baltimore, Md., Sep. 26, 2006). Thus, misincorporation of Aze into HIF proteins can interfere with the hydroxylation, and therefore the activity of HIF, including its interactions with other critical proteins, such as pVHL, which may lead to various disorders.

e. Profilins

Profilins regulate the assembly of actin and thus participate in cell motility and help determine cell shape. One type of profilin is found in brain cells. Profilins modulate the equilibrium between G-actin monomers and F-actin polymers. Their function depends upon an interaction with specific polyproline helices containing a motif with five or more consecutive prolyl residues. (Holt and Koffer, Cell motility: proline-rich proteins promote protrusions. Trends Cell Biol., 2001, 11:38-46). Profilins play a central role in chemotactic responses, cell division, embryogenesis, and neuronal differentiation. Therefore, misincorporation of Aze into profilins could have dramatic effects on the structure and function of these proteins resulting in a host of possible disorders.

f. Vesicular Glutamate Transporters

Another class of proline-rich proteins are the vesicular glutamate transporters. These are involved in the regulation of the amount of glutamate in a synapse. Glutamate is the main excitatory neurotransmitter in the central nervous system (CNS); glutamate transporters are used in the CNS to modulate its functioning. Since glutamate does not diffuse across the blood brain barrier, an active transporter is needed. The transporters interact with proteins (endophilins) in excitatory vesicle formation. Therefore, misincorporation of Aze in place of one or more proline residues in a vesicular glutamate transporter protein could negatively affect the transporter's ability to transport glutamate across the blood brain barrier and thereby result in various disorders of the central nervous system due to a reduction in the available amount of glutamate.

g. Myelin Basic Protein

As will be discussed in greater detail below, abnormalities of myelin basic protein, a principal protein of myelin sheaths that insulate axons in the central nervous system, may underlie multiple sclerosis. (See, for instance: Boggs J M, Myelin basic protein: a multifunctional protein. Cell Mol. Life. Sci., 2006, 63:1945-61; Musse et al., Deimination of membrane-bound myelin basic protein in multiple sclerosis exposes an immunodominant epitope, Proc. Natl. Acad. Sci., USA, 2006, 103: 4422-7; and Ridsdale et al., Three-dimensional structure of myelin basic protein. II. Molecular modeling and considerations of predicted structures in multiple sclerosis. J Biol. Chem., 1997, 272: 4269-4275).

A consensually identified epitope of myelin basic protein (residues 90-102) embraces a unique and highly conserved hexapeptide string containing four prolines, three of which are contiguous in the alignment of TPRTPPPSQ (SEQ. ID. NO. 1). The triple proline segment, residues 99-101, has been regarded as a keystone element supporting the overall architecture of the molecule. Aze substitution for prolines in the region could severely alter protein conformation and exert tectonic stress because of the unique torsion angles and steric constraints of the proline analogue. (Tsai et al., Synthesis and peptide bond orientation in tetrapeptides containing L-azetidine-2-carboxylic acid and L-proline. Biopolymers, 1990, 30: 1039-1049). Such effects may influence reciprocal nesting with adjacent molecules. Additional details regarding the implications of Aze misincorporation in myelin basic protein and its putative role in multiple sclerosis is discussed in greater detail below.

h. Potassium Channel Kir4.1

Kir4.1, an ATP-sensitive inward rectifier potassium channel, is expressed in the cell membrane of oligodendrocytes and astrocytes. This channel is important in both maintaining the electrochemical gradient across the cell membrane and in development of oligodendrocytes and myelination (Neusch et al. Kir4.1 potassium channel subunit is critical for oligodendrocyte development and in vivo myelination. J Neuroscience, 2001; 21: 5429-38). Nearly 50% of patients with multiple sclerosis have circulating antibodies against an extracellular domain of Kir4.1 (aa 90-114) that contains the following sequence: AVAHGDLLELDPPAN (amino acids 90-104 of wild type Kir4.1; amino acids 8-22 of SEQ ID NO: 15) (Srivastava et al. NEJM, 2012; 367: 115-123). In this domain, a double proline is flanked by aspartate and alanine residues, both considered “guest” amino acids that may participate in left-handed poly-proline helix (PPII) formation. Aze misincorporation for one of these prolines in Kir4.1 may result in channel dysfunction and/or creation of an immunogenic epitope on the cell surface, resulting in cytotoxicity and cell death.

Proline Substitution and Multiple Sclerosis

Until recently there were only two known natural sources of Aze, sugar beets (*Beta vulgaris*) and Liliaceae. Since humans do not consume sugar beets or lilies as food, Fowden’s observations did not raise concern about human disease, although Aze was subsequently shown to be highly toxic, teratogenic, and capable of being misincorporated into the proteins of numerous species, including our own. The compound has recently been identified in garden or red beets, the vegetable that makes its way to the human table. In some regions garden beets are a mainstay of the diet. The concern about Aze goes beyond table beets, and includes sugar beets as well. Their by-products may be inundating regions of Europe and North America. It is difficult to determine with accuracy the precise quantities, but it is likely that the European Union produces about 25 million tons of sugar annually. This amount requires the yearly harvesting of about 100 million tons of sugar beets containing about 70,000 kilograms of Aze. Beets belong to the goosefoot family (Chenopodiaceae). Aze has not been found thus far in the two other members of this family, spinach (*Spinacia oleracea*) and Swiss chard (*Beta vulgaris* var. *flavescens*). There may be other natural vehicles that produce or disperse Aze; further studies are needed to determine its distribution in nature.

Sugar is extracted from shredded beets by boiling, evaporation, and crystallization. The residue is processed into beet molasses and then into various protein-containing pulp by-products, which are fed to cattle, sheep, and pigs. In this way the highly noxious nonprotein amino acid, Aze, can enter the food chain, including dairy products.

The clinical expression of many autoimmune disorders requires the presence of an environmental agent exerting its effects on genetically susceptible individuals. The long latency period characteristic of most autoimmune diseases presents a confounding factor. In the case of multiple sclerosis, the risk of developing the disease appears to be strongly influenced by the location of the individual’s residence during childhood, a factor that may outweigh the importance of genetic predisposition.

There is a tight fit between the worldwide prevalence of multiple sclerosis and the geography of beet agriculture. This correlation goes beyond the occurrence of multiple sclerosis in higher latitudes. Beets share this cartography, but their adaptability allows them to flourish under more temperate conditions, such as those of the Mediterranean littoral. In each high-prevalence cluster of cases of multiple sclerosis, beets are a principal commodity or dietary staple. This specification applies to Sardinia, the Orkney Islands, the Middle East, Finland, the Faroe Islands, Alberta, and the Tokachi province in Hokkaido. Tokachi province has the highest rate of multiple sclerosis reported to date in Orientals. Although its population constitutes only 0.3% that of Japan, it produces 45% of Japan’s sugar beets. Alberta is the Canadian epicenter for both sugar beet agriculture and for the prevalence of multiple sclerosis.

Alberta is significant in another way. It was in this province that an outbreak of enzootic ataxia (swayback) occurred in newborn lambs; the neurological manifestations included prostration, head shaking, ataxia, trembling, swaying of the hind quarters and collapse of the posterior trunk. Pathologic studies revealed widespread abnormalities of myelin. A salient observation led to the report that the ewes and the affected offspring had been fed sugar beet silage during pregnancy, lambing, and lactation. This observation is consistent with the concept that proline replacement by Aze, derived from consumption of beets, may cause changes in the topology and charge distribution of myelin. Such alterations can result in dysgenesis, dysfunction, local inflammation, and subsequent autoimmune responses. They also suggest that lambs may be a suitable animal model for the study of multiple sclerosis, including investigations of the effects of feeding Aze. Swayback has been attributed to viruses, copper deficiency, and autoimmune responses to myelin degeneration, but none of these proposals has been validated. Diseases resembling swayback have been reported in various forms of wildlife. The grazing habits of such animals may reveal new plant sources of Aze, although fodder beets are widely available.

There may be other plants or natural vehicles that produce or disperse Aze. Further studies are needed to determine its distribution in nature. In wheat, Aze is a central molecule in a putative methionine cycling biosynthetic pathway involved in the uptake of insoluble iron from soil. Thus, wheat and other gramineous plants may have an endogenous source of Aze, as well as environmental exposure to it. The proline-rich wheat protein, gluten, implicated in celiac disease, is a vulnerable target for Aze misincorporation. The allergenic peptide of gluten contains 30 amino acids, of which 8 are prolines.

The putative role of Aze should be interpreted in the light of the well-established role of immunogenetic susceptibility. In the present context, predisposition to disease could be owing to many factors, including, among others, dysfunction of tRNA, ribosomes or miRNA, the replacement, positioning or the disposition of misassembled proteins, or abnormalities of the immune system.

There are molecular as well as geographic hot spots for multiple sclerosis. In regard to myelin basic protein, proline-rich sequences are sites of vulnerability, loci in which Aze substitution for proline may result in disease-causing epitope formation. A triple proline chain may be a structure especially vulnerable to deformation. As discussed above, the unique torsion angles of Aze peptide bonds may alter the contour of molecules in which the compound is misincorporated. As will be presented in greater detail below, aspects of the present disclosure provide methods and systems for testing for Aze in host proteins and testing for host antigenicity to host peptides containing Aze, which could be implicated in disorders including, but not limited to, various auto-immune disorders including multiple sclerosis. Due to the putative role of Aze in a variety of disorders, such as those discussed above, it is important to limit the amount of Aze consumed by humans and animals, particularly animals that provide sources of food consumable by humans. Therefore, tests, such as those described below are needed for detecting the presence of Aze in food, food precursors, and food byproducts.

Tests for the Presence of Azetidine-2-Carboxylic Acid

Tests for the detection of azetidine-2-carboxylic acid in tissues, lesions, foods and/or food byproducts, among other materials, include, but are not limited to, those intended for use by trained personnel working in laboratories, and those intended for use by producers, distributors, sales personnel or consumers who wish to test products for the presence of azetidine-2-carboxylic acid at the point of production, distribution, sales, consumption or exposure.

The present disclosure provides methods and systems for detecting Aze in food consumable by humans or animals, such as, but not limited to, beets and beet byproducts. In particular, methods of detecting Aze in food produced from an animal (e.g., livestock) fed materials containing Aze (e.g. sugar beet byproducts) are provided. When such animals are fed Aze-containing materials, that Aze may be passed on to humans or other animals fed food produced from such animals, such as eggs, milk, beef, pork, and poultry. Furthermore, additional embodiments include methods of detecting Aze in yeast, since yeast is produced using sugar beet byproducts (e.g., molasses). Any food, food precursor, or food byproduct suspected of being linked to Aze can be tested according to the methods and systems of the present disclosure.

Some exemplary methods of the present disclosure for testing for the presence of Aze in food or host samples (e.g., tissues, sera) include using spectroscopy and chromatography, and other chemical analysis techniques known to those of skill in the art, now known or to be developed. Exemplary methods of using spectroscopy and chromatography for detecting Aze in food are provided in Example 1 below.

Tests for detecting Aze provided in the present disclosure can also be based on methods such as antibody recognition, chromatography, and mass spectrometry. In one embodiment, a test for the presence of Aze in a sample includes an antibody to Aze. In one embodiment of the present disclosure, a kit for testing for the presence of Aze includes an antibody to Aze bound to a solid support (e.g., polystyrene beads in the form of latex) for use in a standard latex agglutination test (LAT) for Aze. When contacted with a sample containing antigenic material (e.g., a sample containing Aze), the beads will agglomerate, causing a change in appearance that can be detected. Other diagnostic assays, known to those of skill in the art, can also be used with Aze antibodies for the detection of Aze. Such assays include, but are not limited to, enzyme immunoassays (EIA), enzyme-linked immunoassays (ELISA), and radioimmunoassays. Such assays are performed using standard methods known to those of skill in the art, such as described in U.S. Pat. Nos. 5,225,331, 5,223,410, 5,741,652, and 6,510,023, which are hereby incorporated by reference. Antibodies to Aze for use in such assays and assay kits can be produced by methods known to those of skill in the art.

In one embodiment, polyclonal antibodies to Aze can be produced by inoculating a host (e.g., a rabbit, goat, mouse, and the like) with a composition including Aze; testing for the presence, at a desired level, of antibodies specific for Aze; collecting sera or other body fluids (e.g., cerebrospinal fluid (CSF)) containing Aze antibody from the inoculated host; obtaining purified polyclonal antibodies to Aze by passing the sera over a column including bound Aze; and eluting the purified anti-Aze antibodies. Such methods are known to those of skill in the art, and are described for example in U.S. Pat. No. 5,610,023, which is hereby incorporated by reference.

Other methods, known to those of skill in the art, for producing monoclonal and/or polyclonal antibodies can be used to produce anti-Aze antibodies for use in testing for the presence of Aze in a sample of interest. Such methods are known to those of skill in the art, and are described for example in U.S. Pat. Nos. 5,225,331, 5,223,410, 5,741,652, and 6,510,023, which are hereby incorporated by reference. A sample of interest to be used in the assays described above may include samples from an organism suspected of containing Aze, such as tissue or fluid samples, or the sample may include a food or food-product suspected of containing Aze.

The present disclosure also includes methods of testing for the presence of Aze using Aze-toxicity screens in bacterial strains sensitive to Aze (e.g., Aze-susceptible strains of *E. coli*), by methods known to those of skill in the art. Also included in the present disclosure are methods for detecting/testing for Aze using tests based on standard analytic chemistry, such as screening for Aze based on differential water/ethanol solubility and optical activity, based on known properties of Aze, such as those presented for Aze in the Merck Index, 1996, $12^{th}$ Ed, p. 156, cmpd. 940, which is hereby incorporated by reference herein.

Tests to Determine Susceptibility to Disease Caused by Azetidine-2-Carboxylic Acid The present disclosure also includes methods and compositions for determining the susceptibility of a host to diseases or conditions (such as autoimmune disorders) mediated by and/or associated with Aze.

Such tests detect increased susceptibility to deleterious effects of azetidine-2-carboxylic acid. Such tests can address immune mechanisms, such as HLA or related immunologic markers. (Online Mendelian Inheritance in Man, OMIM™. Johns Hopkins University, Baltimore, Md., MIM Number 126200: Feb. 9, 2005).

Other tests detect impaired fidelity in translation mechanisms, involving misincorporation of a non-protein amino acid in place of a protein amino acid or the inappropriate insertion of a protein amino acid in place of another. Such tests identify abnormalities involving tRNA, tRNA synthetases, and ribosomal constituents.

Such tests can include tests to detect the presence of Aze in host proteins (such as by using the tests and kits described above) as well as tests to detect/determine the presence of antibodies to Aze-containing antigens that may be the cause and or a mediator of disease (such as described below). Various host organisms can be tested, from cows, goats, and sheep, to humans.

Lambs present a good model for the investigation of the effects of Aze, due to the presence of the disorder enzootic atazia (swayback), as discussed above, which may be linked to an autoimmune response to myelin degeneration, which may be linked to Aze incorporation in myelin.

Tests to Detect the Presence of Antibodies or Other Cellular Immune Responses to Antigens Containing Azetidine-2-Carboxylic Acid The present disclosure includes methods and compositions for determining antigens that mediate autoimmune response in patients with auto-immune disease. Due to the strong links between Aze and the prevalence of autoimmune diseases, it is believed that such antigens will include Aze.

Since not every person or host exposed to Aze will contract an autoimmune disease, the disease also likely involves a genetic component. The genetic component may include, for instance, a break-down in the cellular mechanisms for correcting mis-incorporation of Aze (and/or other non-protein amino acids) or an immune system particularly sensitive to the presence of non-protein amino acids, such as Aze, in host proteins. Thus, the present disclosure includes methods for detecting Aze in host polypeptides as well as detecting an immune response to antigens containing Aze (e.g., the presence of antibodies to peptides, such as host peptides or portions thereof, containing Aze).

One embodiment includes detecting Aze in host polypeptides to confirm misincorporation of Aze in host polypeptides. The host may be a healthy host or a host with a disorder with a putative association with Aze misincorporation, such as multiple sclerosis. Aze present in host proteins may be detected in a number of ways, such as by spectroscopy, as demonstrated in Example 2, where peak shifts can be seen representing the presence of Aze instead of proline (see FIG. 4).

In other methods, antibodies to Aze can be used to detect polypeptides containing Aze in a host sample. An exemplary embodiment includes obtaining a sample from a host, where the sample includes host polypeptides and contacting the host sample with a composition including at least one anti-Aze antibody, where the at least one anti-Aze antibody recognizes at least one host polypeptide having Aze in place of proline in the polypeptide sequence.

The present disclosure also includes methods of detecting anti-Aze antibodies. Such antibodies can then be used for screening for Aze-containing antigens in a host and for diagnosing disorders associated with Aze misincorporation by recognizing the Aze containing antigen in the host. Methods of detecting anti-Aze antibodies can also be used to diagnose disorders associated with Aze by detecting the anti-Aze antibodies in a host sample.

One embodiment of the present disclosure includes detecting antibodies to Aze in a host. This provides the ability to determine if certain hosts (e.g., hosts with certain disorders, such as multiple sclerosis or other auto-immune disorders, among others) harbor anti-Aze antibodies that can serve as an indicator of disease state, thereby providing antibodies for a diagnostic test. In an embodiment of a method of detecting antibodies to peptides including Aze in a host, a host sample is provided that contains host antibodies (e.g., blood, saliva, urine, sera, cerebro-spinal fluid, etc.). At least one test peptide (or a mixture of test peptides or a mixture of test and control peptides) is provided, where the test peptide(s) is a derivative of a wild-type peptide having at least one proline residue replace by Aze (e.g., SEQ ID NOs: 2-8, 10, 11, 12, 13, 14, 16, 17, and 18). In a particular example the host has multiple sclerosis and the test peptide is a portion of the sequence of myelin basic protein or Kir4.1 having proline residues with one or more proline residues replaced by Aze. The host sample is contacted with the test peptide(s) and examined for detecting any binding between the test peptide(s) and any antibody from the host sample, where binding indicates the presence of an antibody to the Aze containing peptide. Methods known to those of skill in the art can be used to detect binding, such as by using well-known reporter molecule systems (e.g., fluorescent dyes, and other detectable labels).

In particular embodiments, the host has or is suspected of having an autoimmune disorder and samples from the host are tested for affinity to Aze and/or Aze containing antigens. Such affinity tests are known to those of skill in the art. For instance, Aze and/or Aze-containing antigens can be bound to a solid support (e.g., in a column), a sample containing sera or CSF (cerebro-spinal fluid) from a host with an autoimmune disorder (such as multiple sclerosis) can be contacted with the column, the column can be washed, and then any bound antibody can be eluted and analyzed.

In embodiments of the methods of detecting antibodies to peptides including Aze, the method also includes providing at least one control peptide having the same amino acid sequence as the test peptide, except that the control peptide has a wild-type sequence without any Aze incorporated into the peptide. Then the control peptides are also contacted with the host sample (separately from or in the same sample as the test peptides) and the sample is examined to detect any binding between the control peptide and any antibody from the host sample. The binding between the (a) test peptides and antibodies of the host sample can be compared with the binding between (b) the control peptides and antibodies from the test sample. The difference between (a) and (b) is then determined to provide additional information about the host sample and the host. For instance, in embodiments, when (a) is greater than (b) it indicates that the host has a condition or a predisposition for a condition associated with mis-incorporation of Aze in host proteins (e.g., multiple sclerosis and other auto-immune disorders discussed above. In embodiments, the control peptide is a portion of a protein selected from MBP or Kir4.1 and a value of (a) above greater than (b) indicates the host has multiple sclerosis or a predisposition for multiple sclerosis. In the above-described embodiment, when (a) is greater than (b), the method may also include conducting additional diagnostic tests for multiple sclerosis in the host.

In embodiments of the methods of detecting antibodies to peptides including Aze where the sample is from a host having multiple sclerosis, the test peptide including Aze can have a sequence corresponding to a portion of the sequence of a MBP protein and having at least one proline residue replaced by Aze, such as but not limited to a peptide with the amino acid sequence selected from SEQ ID NOs: 2-8, 10, 11, 12, 13, and 14. In other embodiments of the methods of detecting antibodies to peptides including Aze where the sample is from a host having multiple sclerosis, the test peptide including Aze can have a sequence corresponding to a portion of the sequence of a potassium channel Kir4.1 protein and having at least one proline residue replaced by Aze, such as but not limited to a peptide with the amino acid sequence selected from SEQ ID NOs: 16, 17, and 18.

The present disclosure also includes methods of screening a library of peptides containing Aze for antigenicity. Such methods include detecting antibodies to Aze-containing peptides by providing a library of test peptides having Aze in place of at least one proline residue. The library of peptides is contacted with a composition that includes one or more antibodies. The composition may include a known antibody or a known mixture of antibodies, or the composition may include unknown antibodies. Furthermore, the sample may be a sample from a host that contains host antibodies (e.g., blood, serum, saliva, urine, cerebro-spinal fluid, or other sample). Then the Aze-peptide library and the antibody sample are examined to determine if any binding has occurred between the peptides and an antibody present in the antibody composition, where detection of binding indicates the presence of an antibody to an Aze-containing peptide in the library. In exemplary embodiments, the library of test peptides includes one or more peptides selected from the peptides of SEQ ID NOs: 10, 11, 12, 13, 14, 16, 17, and 18 described herein. The library may include peptides having partial sequences of one or more of the following human proteins, where the wild-type sequence has at least one proline residue that has been replaced by Aze: myelin basic protein, potassium channel Kir4.1, collagen, hypoxia-inducible factor, profilins, ion channel proteins, vesicular glutamate transporters, and hemoglobins. In embodiments, the library of test peptides includes one or more peptides having amino acid sequences corresponding to a portion of a wild-type sequence of one or more human proteins associated with an auto-immune disorder, where the wild-type sequence of each protein portion includes at least one proline residue and where at least one proline of each corresponding test peptide in the library has been replaced by Aze. In some such embodiments, the auto-immune disorder is multiple sclerosis. In embodiments, the human protein associated with an auto-immune disorder is selected from MBP and Kir4.1.

In embodiments the methods above further include isolating the antibody that binds to the test peptide for identification and/or further study. Such anti-Aze antibodies can be used in methods of the present disclosure described herein.

Binding between the Aze-containing peptides in the library and an antibody in the antibody-containing composition can be detected by any number of methods known to those of skill in the art, such as by the use of fluorescent labels or other detectable labels. Library screening may be performed on a solid support such as a column or an array. An array format may be particularly suitable to screening a large library of potential peptide antigens.

In an embodiment, a library of Aze-containing antigens (e.g., short Aze-containing peptides) can be labeled with a signal molecule having a detectable signal (e.g., a fluorescent dye molecule). A solution containing a sample from a host with an autoimmune disorder can then be contacted with a composition containing one or more labeled Aze-containing antigens, and association of one or more of the antigens with an Aze antibody in the host sample can be determined by detection of the signal molecule.

In particular, the present disclosure includes methods including providing a library of Aze-containing peptides and testing said peptides for antigenicity. In preferred embodiments, the Aze-containing peptides are relatively short peptides (e.g., from about 9 to about 50 amino acids long, from about 9 to about 30 amino acids long, etc.) having a sequence corresponding to a segment of a wild-type protein including at least one proline residue, where the Aze-containing peptide contains at least one Aze in place of at least one proline. Thus, an exemplary library would contain several peptides having Aze incorporated in place of proline. The peptides (e.g., potential antigens) can be chemically synthesized or produced in biologic systems by methods known to those of skill in the art.

In particularly preferred embodiments, the library of test peptides is prepared from proteins and/or peptides believed to be implicated in autoimmune diseases, such as, but not limited to, myelin, collagen, and elastin. Preferably such proteins or peptides also have a long half-life and are proline rich. It is known that myelin, a neuronal protein, is attacked by the immune system of patients with multiple sclerosis, but it is not known if this attack is mediated by the myelin itself or another protein. In embodiments, the present disclosure provides libraries of test peptides made of fragments of the myelin basic protein (MBP) and/or Kir4.1 protein, in which one or more prolines are substituted with Aze. Of interest is the sequence spanning amino acids 91-104 of the myelin basic protein, in particular the fragment that represents amino acids 95 to 103 of wild type myelin basic protein and has the sequence TPRTPPPSQ (SEQ. ID. NO. 1). For instance, exemplary peptides would have one or more of the prolines of the above sequence replaced by Aze (Az). Exemplary derivatives of this wild-type peptide include, but are not limited to, the following sequences: TAzRTPPPSQ (SEQ. ID. NO. 2), TPRTAzAzAzSQ (SEQ. ID. NO. 3), TPRTAzAzPSQ (SEQ. ID. NO. 7), and TPRTAzPPSQ (SEQ. ID. NO. 8), among others, as provided below in Table 1.

In other embodiments a peptide of interest includes the fragment spanning amino acids 82 to 105 of MBP and having the sequence DENPVVHFFKNIVTPRTPPPSQGK (SEQ ID NO: 9). For instance, exemplary Aze-containing derivative test peptides would include, but are not limited to the following sequences: SEQ ID NOs: 10-14, (shown in Table 2 in Example 3, below).

In further embodiments, a peptide of interest includes the fragment spanning amino acids 83 to 120 of Kir4.1 and having the sequence GVVWYLVAVAHGDLLELDPPANHTPCWQVHTLTGAFL (SEQ ID NO: 15). For instance, exemplary Aze-containing derivative test peptides would include, but are not limited to the following sequences: SEQ ID NOs. 16-18 (shown in Table 3 in Example 3, below).

As discussed above, collagen contains a very high concentration of proline (nearly 15% of the amino acids in collagen are proline, with proline making up nearly every $3^{rd}$ amino acid in some portions of the sequence); thus, it also represents a particularly good candidate for generating Aze-containing antigen libraries. With the high concentration of proline, a number of potential fragments of collagen, having Aze incorporated in place of one or more prolines, could be used as potential test peptides (e.g., antigens) in the methods above for testing for auto-immune disorders.

The peptide libraries are then tested for antigenicity against samples derived from patients with auto-immune diseases, such as multiple sclerosis, such as by methods described above, and other methods known to those of skill in the art (such as those that can be used to screen for an affinity between members of the peptide library of potential antigens and antibodies present in hosts with auto-immune diseases).

Thus, the present disclosure includes the antigens and antigen libraries described above, as well as the methods described above for screening for antigenicity to antibodies of patients with auto-immune disorder. Positive antigens (e.g., antigens screening positive for antigenicity in patients with auto-immune disorder, and particularly antigens that are positively identified as a specific target in one or more auto-immune disorders) can then be used to screen other patients/hosts for the presence of such antibodies. The methods can be used to screen patients/hosts for the existence of or a predisposition to various auto-immune diseases.

Samples to be used in such screening tests include, but are not limited to, tissues, lesions, blood, blood components (including cells), urine, cerebrospinal fluid, and other biologic fluids or samples from humans or other animals.

The present disclosure also includes the Aze-containing antigens themselves. Such antigens (e.g., Aze-containing peptides) can be used as diagnostic and research tools as described above, to detect anti-Aze antibodies and aid in the diagnosis of disorders. Exemplary peptides include isolated and/or synthesized polypeptides having a sequence selected from SEQ. ID. NOS. 2-8, described herein. The present disclosure also includes antibodies capable of binding a polypeptide including a sequence selected from SEQ. ID. NOS. 2-8. Embodiments of the present disclosure also include isolated and/or synthesized polypeptides having a sequence selected from SEQ. ID. NOS. 10-14, described herein. The present disclosure also includes antibodies capable of binding a polypeptide including a sequence selected from SEQ. ID. NOS. 10-14. Embodiments also include isolated and/or synthesized polypeptides having a sequence selected from SEQ. ID. NOS. 16-18, described herein. The present disclosure also includes antibodies capable of binding a polypeptide including a sequence selected from SEQ. ID. NOS. 16-18.

Methods of the present disclosure also include methods of detecting Aze in host polypeptides, such as by using antibodies to Aze-substituted peptides. In embodiments, methods of detecting Aze in host polypeptides include obtaining a sample from a host, where the sample includes host polypeptides, and contacting the host sample with a composition including at least one anti-Aze antibody, where the at least one anti-Aze antibody recognizes at least one host polypeptide having Aze in place of proline in the polypeptide sequence. In embodiments, the anti-Aze antibody can be an antibody identified by one or more of the methods of the present disclosure described above for detecting antibodies to peptides including Aze. In embodiments, the anti-Aze antibody for use in the methods of the present disclosure can be an antibody capable of binding an Aze-substituted polypeptide including an amino acid sequence corresponding to the wild-type amino acid sequence of a human protein associated with an auto immune disorder (such as but not limited to multiple sclerosis), where the amino acid sequence of the Aze-substituted polypeptide contains at least one Aze in place of a proline in the corresponding wild type peptide. In embodiments, the Aze-substituted polypeptide has a sequence selected from: SEQ ID NOs: 10, 11, 12, 13, 14, 16, 17, and 18.

The specific examples below are to be construed as merely illustrative, and not limitative of the remainder of the disclosure in any way whatsoever. Without further elaboration, it is believed that one skilled in the art can, based on the description herein, utilize the present disclosure to its fullest extent. All publications recited herein are hereby incorporated by reference in their entirety.

It should be emphasized that the above-described embodiments of the present disclosure, particularly, any "preferred" embodiments, are merely possible examples of the implementations, merely set forth for a clear understanding of the principles of the disclosure. Many variations and modifications may be made to the above-described embodiment(s) of the disclosure without departing substantially from the spirit and principles of the disclosure. All such modifications and variations are intended to be included herein within the scope of this disclosure, and the present disclosure.

The following examples are put forth so as to provide those of ordinary skill in the art with a complete disclosure and description of how to perform the methods and use the compositions and compounds disclosed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. In an embodiment, the term "about" can include traditional rounding according to significant figures of the numerical value.

EXAMPLES

Now having described the embodiments of the methods, compositions, systems and features of the present disclosure in general, the following examples describe certain embodiments of compositions and methods for detection of Aze in food and embodiments of compositions and methods for Aze containing antigens for use in detection of antibodies to Aze containing proteins and peptides. While such embodiments are described in connection with Examples 1-4 and the corresponding text and figures, there is no intent to limit the embodiments of the present disclosure to these descriptions. On the contrary, the intent is to cover all alternatives, modifications, and equivalents included within the spirit and scope of embodiments of the present disclosure.

Example 1

Azetidine-2-Carboxylic Acid in Milk and in Yeast

As discussed above, Aze is present in table beets and in sugar beets; the latter are the source of about 30% of the world's supply of sucrose. Byproducts of sugar beets leftover from sugar processing are fed to meat and dairy livestock, and in this way their constituents may enter food consumed by humans. The purpose of this example was to determine whether Aze is present in certain foods derived from such livestock and then consumed by humans.

This example presents the results of amino acid analyses of two groups of foods. The first were chosen because they are derived from animals that may have been fed sugar beet byproducts; the second were foods chosen because they have no apparent exposure to sugar beet byproducts.

In addition, two varieties of commercial baker's yeast (*Saccharomyces cerevisiae*) were examined for Aze content. Yeast was included in this study inasmuch as this organism has potential exposure to Aze in sugar beet molasses, which is widely used as a major raw material in yeast production.

Results and Discussion

The analyses were done on food products purchased at random at four different supermarkets located on the San Francisco Peninsula.

Figure 2:
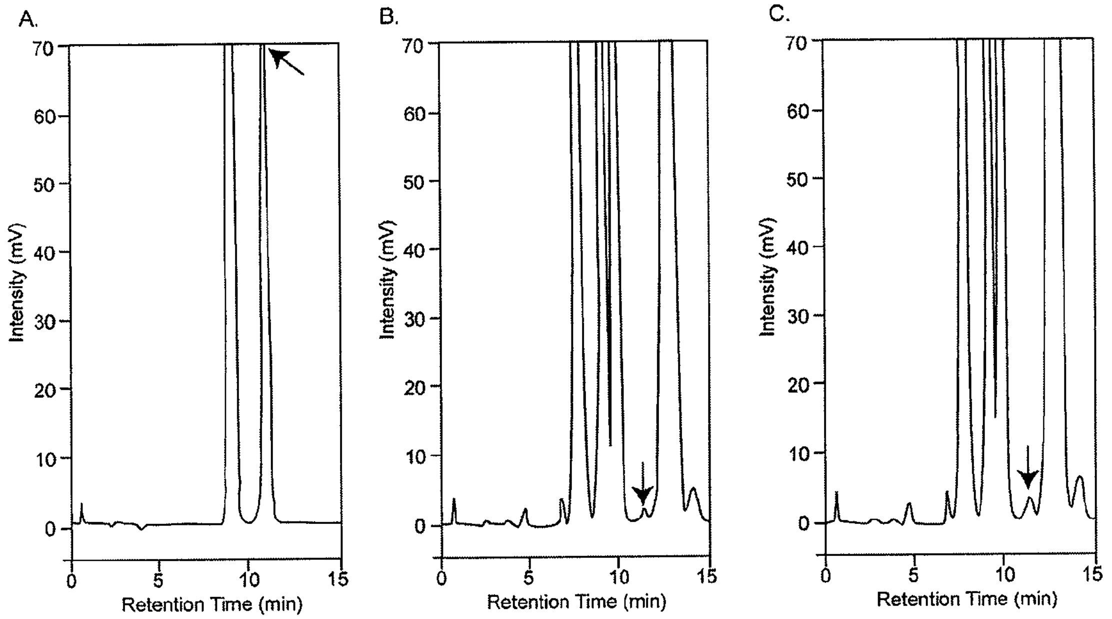
FIG. 2 illustrates chromatographic peaks of (A) pure Aze, (B) liquid milk, and (C) liquid milk spiked with Aze, using a Hitachi L-8800 amino-acid analyzer.

Aze was found to be present in each of two different samples of pooled milk, one a canned fat-free liquid variety, and the other a powdered fat-free dry milk variety, provided by two different suppliers. The findings were confirmed using two different analytic systems, the first a Beckman 6300 amino-acid analyzer, and the second a Hitachi L-8800 amino acid analyzer, as shown in FIG. 2. The concentration of Aze in liquid milk was 0.4 mM.

Figure 3:
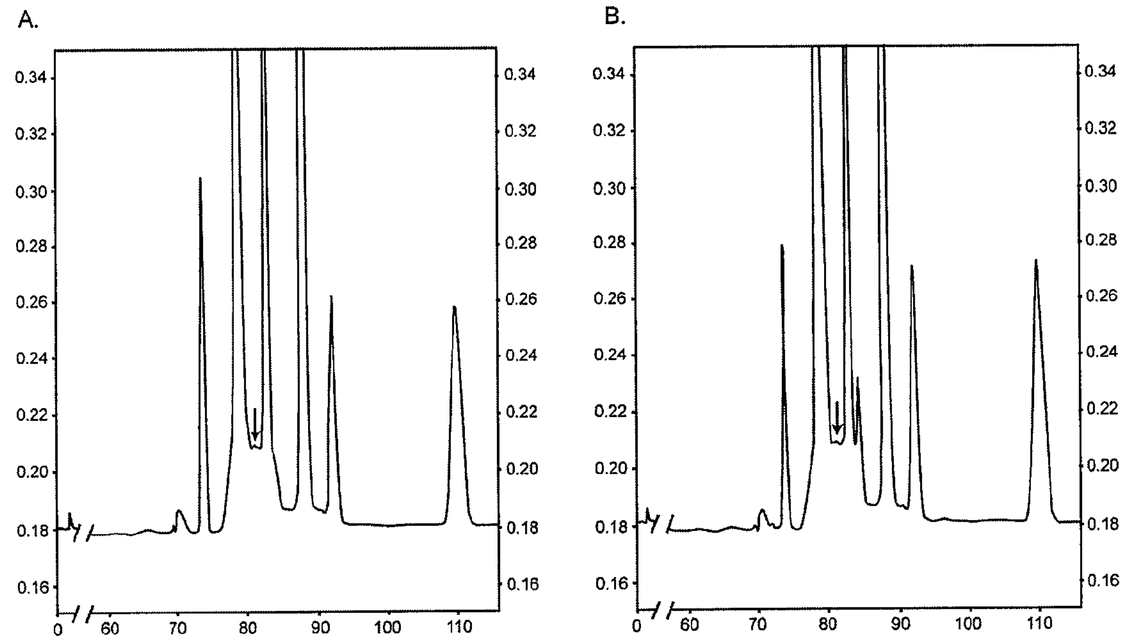
FIG. 3 illustrates chromatographic peaks of two different varieties of yeast (*Saccharomyces cerevisiae*), samples A and B, showing the peaks of Aze in each. The analyses were done using a Beckman (Li) amino-acid analyzer.

This approach was used on two different samples of commercial baker's yeast, one produced in Canada and the other in Mexico. The same two analytic systems were used and in each case Aze was found in *Saccharomyces cerevisiae*, as shown in FIG. 3. The concentration of Aze was 0.08 μM per gram of dry yeast.

The same approach was used for testing potato start, rice flour and tapioca flour. Aze was not found in any of these foods.

These data confirm that Aze is present in bovine dairy products and in commercial yeast. How Aze enters milk is not established. While not wishing to be bound by theory, it is believed that the source may be sugar beet byproducts fed to the livestock. Prospective studies of milk derived from cattle whose diets contain or do not contain sugar beet byproducts can address this issue. Similar studies of yeast can also be performed.

As discussed in detail above, the intrusion of Aze into the food chain has significant implications regarding disease in humans. The misincorporation of Aze in place of proline may be especially pathogenetic when the malformed protein is involved in critical functions such as DNA repair or embryogenesis.

These data indicate that azetidine-2-carboxylic acid is present in dairy products and in yeast. It is believed that entry of this highly toxic and teratogenic nonprotein amino acid into the human food chain relates to the use of sugar beet byproducts as supplemental feed for livestock.

Materials and Methods

The powdered materials (tapioca flour, rice flour, potato starch, nonfat dry milk) and dry samples (e.g., yeasts) were stored at ambient temperature either in the original packages (e.g., dry milk, yeast) or in 15-ml plastic tubes. The canned liquid fat free milk was transferred into two 1.5 ml Eppendorf tubes and stored at −20° C.

All samples were sent for amino acid analysis by 2-day commercial land-based carrier at ambient temperature. All were shipped dry either in their original form or when appropriate after freezing and lyophilization. Tapioca flour, rice flour and potato starch were submitted in their original powder form; liquid milk (100 μl) was frozen and lyophilized; powdered milk (10 mg in 100 μl water) was frozen and lyophilized; both yeast samples were slurried (10 mg in 500 μl water) and sonicated (Branson model 5200 bench-top water bath sonicator) for 1.5 hr with occasional vortexing; then frozen and lyophilized.

The samples were transferred into two 200 μl formic acid transfer glass hydrolysis tubes and then dried. Each sample was them subjected to liquid phase hydrolysis (200 μl, 6 N HCl/0.1% phenol @ 110 C for 24 hrs), and then dried. Each sample was then dissolved in aminoethyl cysteinyl (AE-Cys) dilution buffer, vortexed, centrifuged, and 50 μl containing 5.0 nmol of the added AE-Cys was loaded in an amount of 50 μl, containing 5.0 nmol of the added AE-Cys.

Each sample was analyzed twice, using two different analytical systems, a Beckman 6300 Li-buffered system and a Hitachi L-8800 (Na-based) machine. A standard injection volume of 50 μl in AE-Cys buffer was used and included norleucine as an internal standard to correct for variations on the operating conditions of the analyzers over time.

Aze remnants were found in the milk and yeast samples using both systems. The same remnants were present in pure Aze samples (Sigma Aldrich catalog #A0760 lot 026K1354; CAS number Aze is 2133-34-8), in Aze-spiked samples, and in milk and yeast samples that were not spiked. The elution times were different for the two analytic systems, 80 minutes for the Beckman system and 11.5 minutes for the Hitachi system. These remnants were not found in any of the other samples. The large difference in elution times indicates the presence of two distinct remnants of Aze in the two analytic systems.

Example 2

Synthesis of Aze-Containing Peptides

In this example a peptide library was prepared, with each peptide nine amino acids in length (to mimic the nonameric antigens that would be presented by a host MHC complex). The following peptides represent derivatives of a nine-amino acid length proline-containing sequence from human myelin basic protein, where one or more of the proline residues has been replaced by Aze. Table 1 below shows the sequence of each peptide. Sequence 1 is amino acids 95 to 103 of wild-type human myelin basic protein, and sequences 2-5 represent derivatives of sequence 1, where one or more of the proline residues have been replaced by Aze.

Peptide Synthesis

Preparation of the above listed peptides (SEQ. ID. NOS: 1-6) was prepared according to established protocol using a Symphony™ peptide synthesizer at the Peptide and Nucleic Acid (PAN) Facility of the Stanford University School of Medicine. The azetidine-2-carboxylic acid used in the synthesis was purchased from ANASPEC, reagent number 20340.

NMR Analysis

Nuclear Magnetic Resonance (NMR) experiments were performed at the Stanford Magnetic Resonance Laboratory (SMRL), a Stanford University School of Medicine research service center. Experiments were performed on a 600 MHz Varian Inova spectrometer equipped with a 5 mm triple resonance H{CN} z-gradient probe and variable temperature control capability, and running VNMR version 6.1C software and the BioPack version 2004-05-13 pulse sequence library.

Peptide samples were synthesized as described above. The peptide sequences provided for NMR analysis are shown in Table 1.

TABLE 1

| SEQ. ID. NO. | Sequence | MW (g/mol) | Mass Provided (mg) |
|---|---|---|---|
| 1 | $NH_2$-T-P-R-T-P-P-P-S-Q-COOH | 980.1 | 1.1 |
| 2 | $NH_2$-T-Az-R-T-P-P-P-S-Q-COOH | 966.0 | 1.0 |

TABLE 1 -continued

| SEQ. ID. NO. | Sequence | MW (g/mol) | Mass Provided (mg) |
|---|---|---|---|
| 3 | $NH_2$-T-P-R-T-Aze-Aze-Aze-S-Q-COOH | 937.79 | 1.0 |
| 4 | $NH_2$-T-Az-R-T-Aze-P-P-S-Q-COOH | 951.89 | 1.1 |
| 5 | $NH_2$-T-Az-R-T-Aze-Aze-P-S-Q-COOH | 937.79 | 1.0 |
| 6 | $NH_2$-T-Az-R-T-Aze-Aze-Aze-S-Q-COOH | 923.69 | 1.2 |

Peptide samples were dissolved into 450 μL of aqueous buffer (10 mM sodium phosphate, 100 mM NaCl, pH 6.5) and 50 μL $D_2O$.

Figure 4:
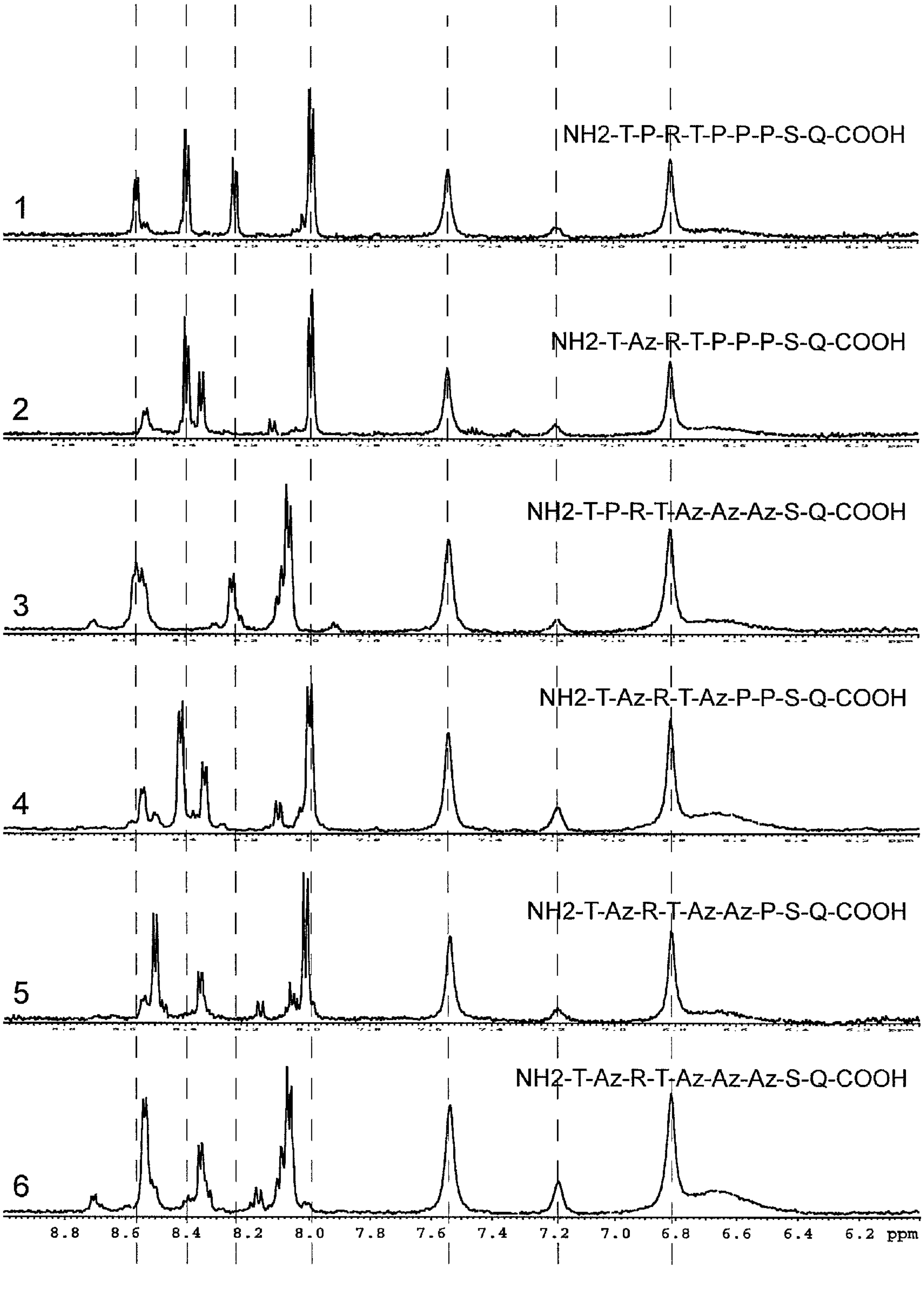
FIG. 4 illustrates NMR spectra of 6 peptide derivatives of myelin basic peptide. Peptide 1 represents amino acids 95 to 103 of a wild-type human myelin basic protein (SEQ. ID. NO. 1). Peptides 2-6 (SEQ. ID. NOS. 2-6) are derivatives of peptide 1 with one or more proline residues replaced with Aze.

One-dimensional proton spectra were collected on each peptide sample at 25° C. using the "water" pulse sequence configured for WET water suppression. Pertinent acquisition parameters utilized were pre-acquisition delay (d1)=1 sec, total data points (np)=8192, number of scans (nt)=16, and spectral width (sw)=8384.86 Hz. Data were processed using 1× zero-filling and an exponential line-broadening (lb) of 1 Hz. The NMR spectra of the six peptides are illustrated in FIG. 4, which is a stacked plot of proton 1-dimensional experiments of the 6 nonameric peptides showing the amide proton region. The vertical dashed lines are aligned with the WT sequence (SEQ. ID. NO. 1) peptide resonances.

Two-dimensional proton spectra were collected on peptide 1 at 25° C. A TOCSY (FIG. 5) was acquired using the "zdipsitocsy" pulse sequence with a mixing time=60 millisec, pre-acquisition delay (d1)=1 sec, direct detected dimension parameters of total data points (np)=8192, number of scans (nt)=16, spectral width (sw)=6000.60 Hz, and indirect detected dimension parameters of number of increments (ni)=256, spectral width (sw1)=6000.60.

A ROESY (FIG. 6) was acquired using the "wroesy" pulse sequence with a mixing time=300 millisec, pre-acquisition delay (d1)=3 sec, direct detected dimension parameters of total data points (np)=8192, number of scans (nt)=16, spectral width (sw)=6000.60 Hz, and indirect detected dimension parameters of number of increments (ni)=256, spectral width (sw1)=6000.60. Data were processed using 1× zero-filling and sine-bell squared apodization functions in both dimensions.

One-dimensional and two-dimensional spectra were also collected on peptide 1 at 15° C. utilizing the same pulse sequences and parameters as at 25° C. except the ROESY pre-acquisition delay was 2 sec, and two additional ROESY experiments (mixings times of 100 and 200 millisec) were acquired. Processing was similar as set forth above. Data is not shown.

Figure 5:
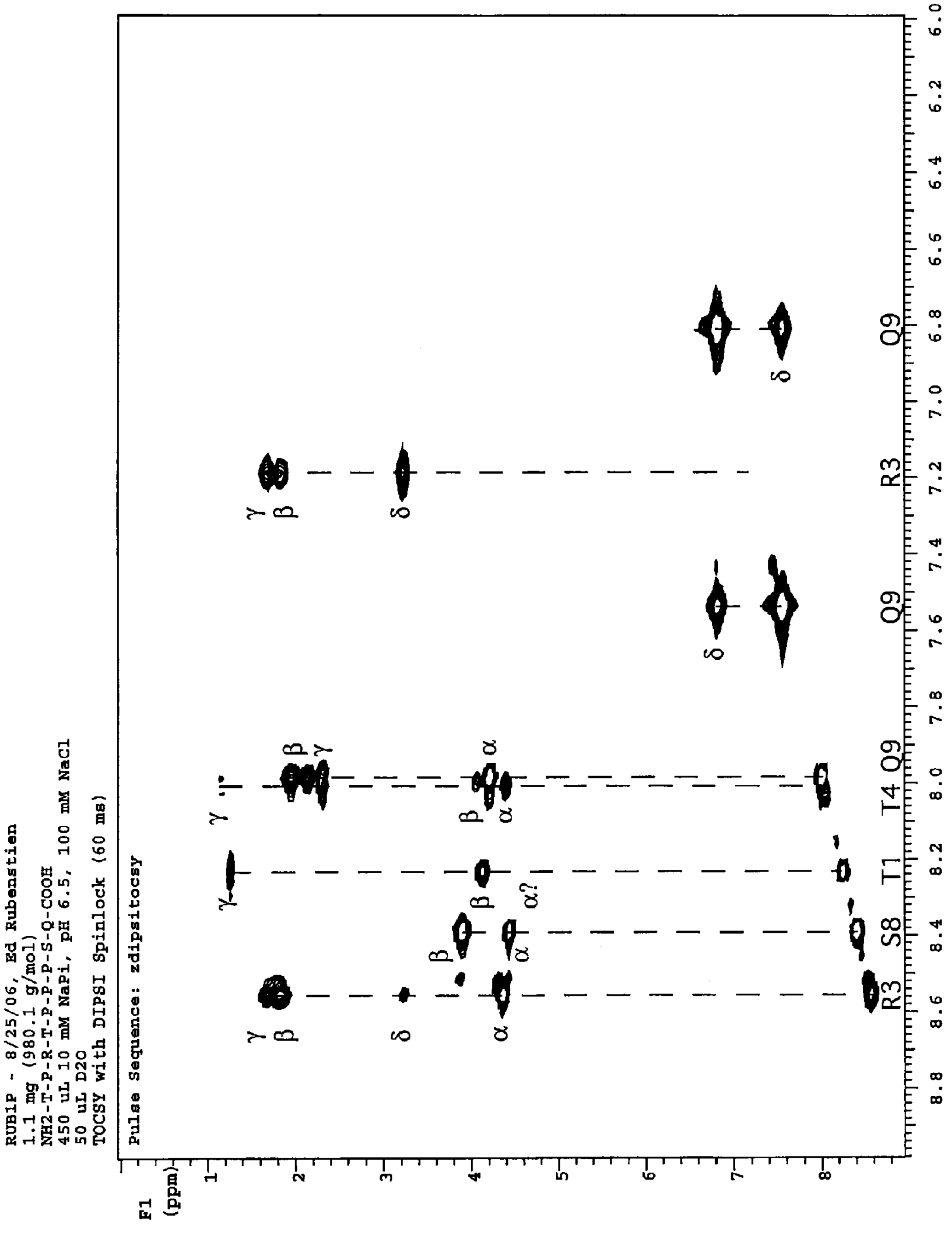
FIG. 5 illustrates a TOCSY two-dimensional proton spectra of peptide 1 (SEQ. ID. NO. 1).
Figure 6:
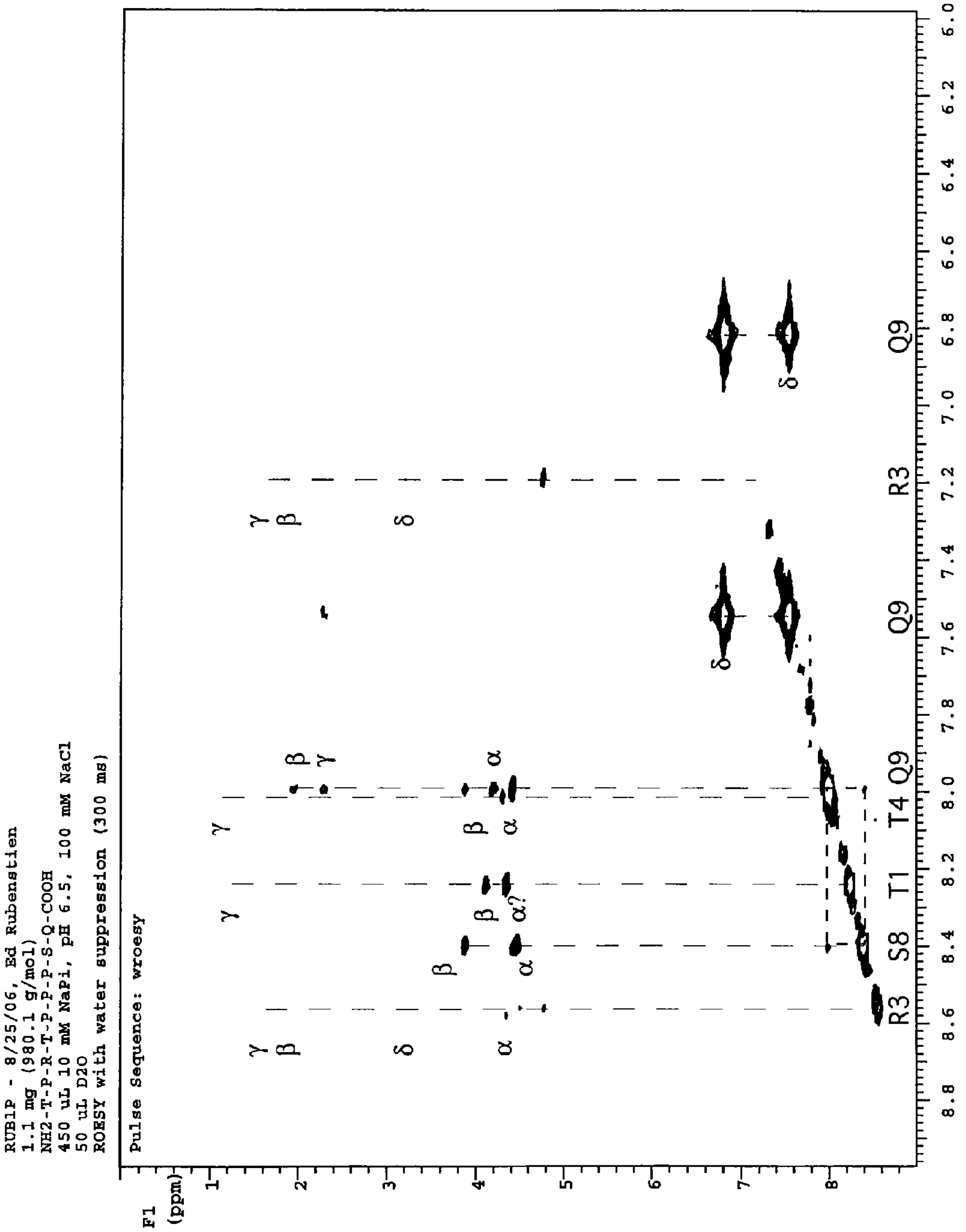
FIG. 6 illustrates a ROESY two-dimensional proton spectra of peptide 1 (SEQ. ID. NO. 1).

FIGS. 5 and 6 illustrate 2-dimensional TOCSY (FIG. 5) and ROESY (FIG. 6) spectra of WT sequence (SEQ. ID. NO. 1) performed at 25° C. Regions shown are the fingerprint regions of the 2-D spectra, consisting of the amide proton region in the F2 (horizontal) dimension and the full spectral range in the F1 (vertical dimension). These spectra were utilized to assign the resonances and are annotated on the figures. Not all side-chain resonances are observed in the ROESY data set likely due to amide proton exchange rates at 25° C., but the resonance assignment labels are carried over from the TOCSY figure.

Example 3

Immunology Studies with Aze-Containing Test Peptides

The present examples describe studies of clinical samples of active multiple sclerosis (MS) patients and age-matched controls evaluating their immune responses to peptides containing azetidine (Aze) in place of proline.

Materials and Methods

The binding of antibodies in clinical samples to peptide sequences from MBP and Kir4.1 were conducted in the following manner: Samples were obtained from 6 MS-active patients collected in Grand Forks, N. Dak., and 4 control samples from Grand Forks, N. Dak. or Stanford, Calif. Blood was collected in heparinized tubes and shipped to the Stanford University Human Immune Monitoring Center, where the samples were processed (separated into plasma and peripheral blood mononuclear cells) and stored at −80 degrees Celsius until thawed for study.

Test peptides (Tables 2 & 3) were synthesized by Genscript, USA, Inc.

TABLE 2

Aze-substituted MBP peptides

| SEQ. ID. NO. | Sequence | Name | N-term |
|---|---|---|---|
| 9 | $NH_2$-DENPVVHFFKNIVTPRTPPPSQGK-COOH | MBP WT (aa 82-105) | Biotin |
| 10 | $NH_2$-DENAzeVVHFFKNIVTPRTPPPSQGK-COOH | MBP Aze 1 | Biotin |
| 11 | $NH_2$-DENPVVHFFKNIVTAzeRTPPPSQGK-COOH | MBP Aze 2 | Biotin |
| 12 | $NH_2$-DENPVVHFFKNIVTPRTAzePPSQGK-COOH | MBP Aze 3 | Biotin |
| 13 | $NH_2$-DENPVVHFFKNIVTPRTPAzePSQGK-COOH | MBP Aze 4 | Biotin |
| 14 | $NH_2$-DENPVVHFFKNIVTPRTPPAzeSQGK-COOH | MBP Aze 5 | Biotin |

TABLE 3

| Aze-substituted Kir4.1 peptides | | | |
|---|---|---|---|
| SEQ. ID. NO. | Sequence | Name | N-term |
| 15 | $NH_2$-GVVWYLVAVAHGDLLELDPPA NHTPCVVQVHTLTGAFL-COOH | KIR WT (aa _) | Biotin |
| 16 | $NH_2$-GVVWYLVAVAHGDLLELDAze PANHTPCVVQVHTLTGAFL-COOH | KIR Aze 1 | Biotin |
| 17 | $NH_2$-GVVWYLVAVAHGDLLELDPAze ANHTPCVVQVHTLTGAFL-COOH | KIR Aze 2 | Biotin |
| 18 | $NH_2$-GVVWYLVAVAHGDLLELDPPA NHTAzeCVVQVHTLTGAFL-COOH | KIR Aze 3 | Biotin |

Various concentrations of the biotinylated MBP and Kir4.1 peptides were dispensed into streptavidin coated wells in multi-array plates acquired from Meso Scale Discovery. Aliquots of the plasma samples were then added to each well, followed by tagged anti-human IgG. The readout was the electrochemiluminescence signal, which was measured using the Meso Scale Discovery platform.

Figure 7:
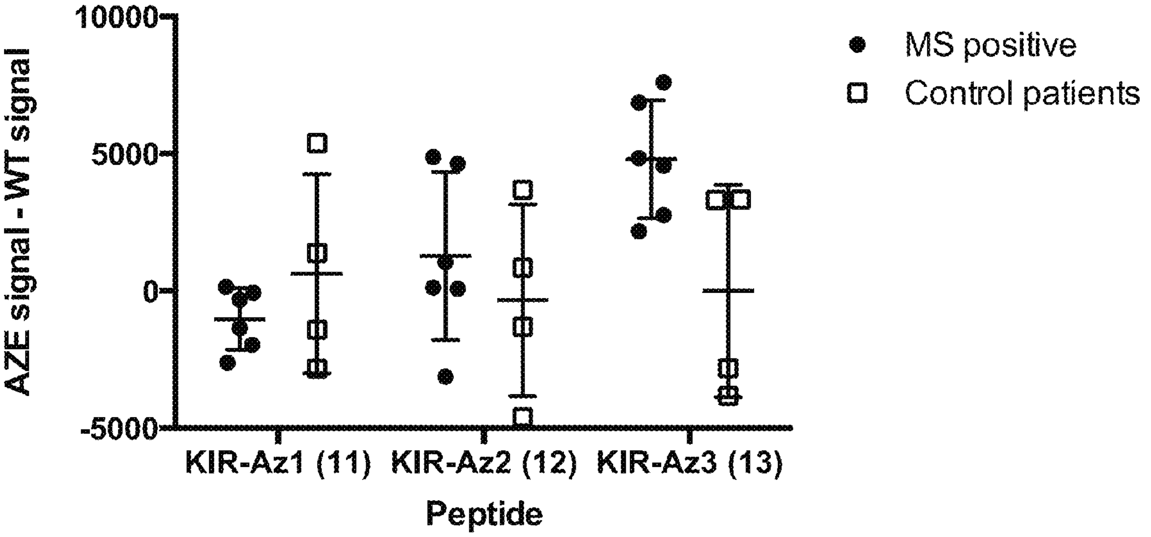
FIG. 7 is a graph illustrating the results of an antibody binding assay with KIR test peptides containing one or more Aze residues in place of proline. The graph shows the difference between the amounts of antibody binding from plasma samples to azetidine-containing peptides over the sequence-matched wild-type peptide control. Notice a higher response in MS-active patients to KIR-Aze3 (13) versus control.
Figure 8:
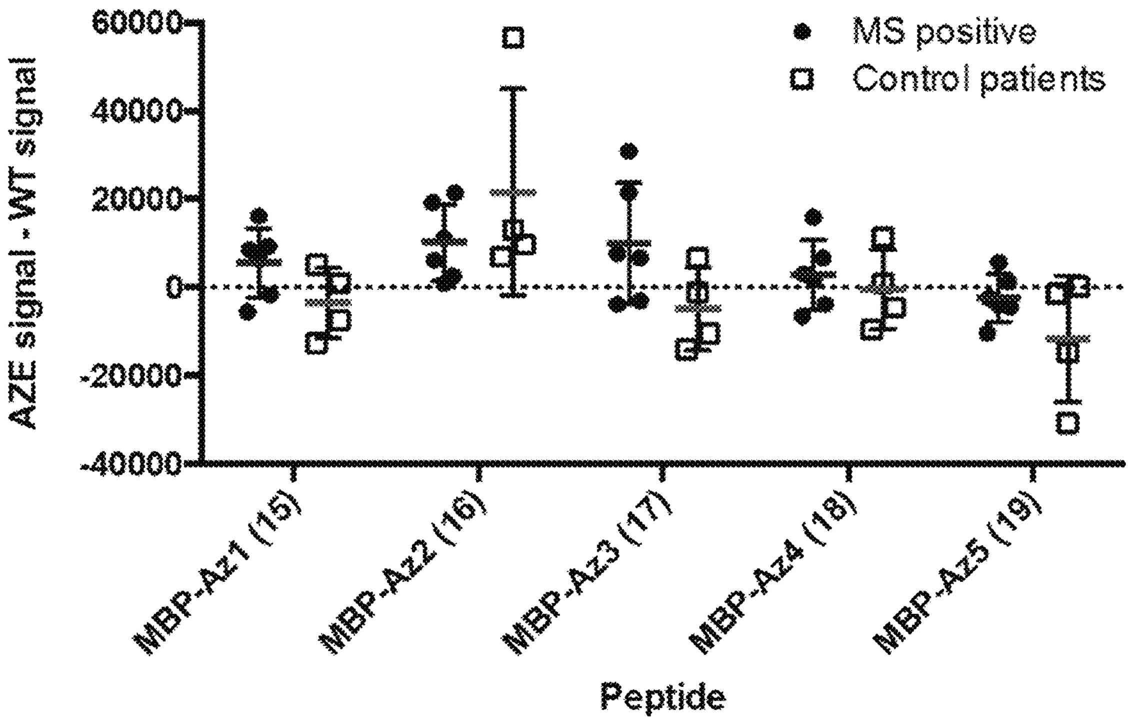
FIG. 8 is a graph illustrating the results of an antibody binding assay with MBP test peptides containing one or more Aze residues in place of proline. The graph shows the difference between the amounts of antibody binding from plasma samples to azetidine-containing peptides over the sequence-matched wild-type peptide control. The group mean response is shown as a bar.

Results:

An Aze-containing peptide from the putative antigenic region of potassium channel Kir4.1 elicited a stronger plasma antibody response than wild-type (proline only) peptide in active-MS patient samples, but not in control samples as demonstrated in the data presented in FIG. 7.

Kir4.1 has been implicated as a target of the autoantibody response in a subset of MS patients (Srivastava R, et al. NEJM (2012) 367; 2: 115-123).

Studies with Aze-containing peptides from the putative antigenic region of myelin basic protein (MBP) were inconclusive (FIG. 2), and the tests are being repeated.

Testing with both MBP and KIR Aze-substituted sequences will be repeated using revised methods.

In addition, preliminary data shows that in peripheral blood mononuclear cells (PBMCs) from patients with multiple sclerosis, Aze-substituted peptide sequences from MBP (Table 1) increased T cell production of interferon gamma (IFNγ) more than the wild-type control sequences (data not shown). PBMCs from control subjects were not stimulated to produce IFNγ by either wild type or Aze-substituted sequences.

Example 4

Azetidine-Induced Oligodendrogliopathy

This example describes studies showing that mice injected or fed azetidine via oral gavage exhibit oligodendrogliopathy in their white matter. The extent of oligodendrocyte swelling and positive staining for DNA-damage increases with increasing amounts of azetidine administered.

The present study demonstrated that Azetidine (Aze) induces a distinct dose-dependent oligodendrogliopathy in outbred CD-1 mice that differs from that induced with other known oligodendrocyte toxins (e.g. cuprizone). Mice were given 300 mg/kg or 600 mg/kg Aze, either by oral or intraperitoneal routes. Both groups show oligodendrocyte nuclear vacuolation and increased microglial reactivity in brain and spinal cord white matter (data not shown). This was not associated with myelin breakdown or other evidence of CNS injury, as assessed by light microscopy and immunohistochemistry. The group of mice receiving the highest does of Aze developed hind limb paresis and had to be euthanized. Gross pathology showed a fatty liver (seen with various toxins)

DNA-damage was assessed by TUNEL staining of spinal cord white matter. The cells also positively stain for Caspase-3, indicating the cells are undergoing apoptosis. There was associated increased oligodendrocyte apoptosis, as detected with TUNEL and caspase-3 stains. Increased major histocompatibility complex I expression was also observed on the apoptotic cells. These results are consistent with Aze misincorporation into cellular proteins and resultant cell stress responses. The oligodendrocyte pathology and microglial activation are similar to those observed in the normal-appearing white matter adjacent to early lesions in MS patients.

The oligodendrogliopathy observed in mice is reminiscent of the microglial activation and oligodendrocyte pathology observed in some MS patients.

We claim:

1. A method of detecting antibodies to peptides comprising Azetidine-2-carboxylic acid (Aze), the method comprising:

providing at least one test peptide comprising Aze, wherein the test peptide is a derivative of a portion of human myelin basic protein or human potassium channel Kir4.1 protein, the test peptide having at least one proline residue replaced by Aze;

providing a sample from a host having multiple sclerosis or suspected of having multiple sclerosis, wherein the sample comprises host antibodies;

contacting the host sample with the at least one test peptide;

detecting binding between the test peptide and an antibody from the host sample;

providing at least one control peptide having the same amino acid sequence as the test peptide, except that the control peptide has a wild-type sequence without any Aze incorporated into the peptide;

detecting binding between the control peptide and an antibody from the host sample; determining a difference in (a) binding between antibodies in the host sample and the test peptide and (b) binding between antibodies in the host sample and the control peptide, wherein, when (a) is greater than (b), determining that the host sample contains antibodies to the Aze containing peptide.

2. The method of claim 1, wherein, a value of (a) greater than (b) indicates the host has multiple sclerosis or has a greater chance of having multiple sclerosis than if (a) was not greater than (b).

3. The method of claim 1, further comprising, when (a) is greater than (b), conducting additional diagnostic tests for multiple sclerosis on the host.

4. The method of claim 1, wherein the test peptide is a derivative of a portion of human myelin basic protein and has an amino acid sequence selected from the group consisting of: SEQ ID NOs: 2, 3, 4, 5, 6, 7, 8, 10, 11, 12, 13, and 14.

5. The method of claim 1, wherein the test peptide is a derivative of a portion of human potassium channel Kir4.1 protein and has an amino acid sequence selected from the group consisting of: SEQ ID NOs: 16, 17, and 18.

6. A method of detecting antibodies to peptides containing Azetidine-2-carboxylic acid (Aze) comprising:

providing a library of test peptides, the library comprising a plurality of test peptides with each test peptide being a derivative of a portion of a protein selected from the group consisting of: human myelin basic protein and human potassium channel Kir4.1 protein, or both, and each test peptide comprising Aze in place of at least one proline residue;

contacting the library of test peptides with a composition comprising one or more antibodies from a host having multiple sclerosis; and detecting binding between a test peptide from the library and an antibody from the antibody composition, wherein binding indicates the presence of an antibody to the Aze-containing peptide.

7. The method of claim 6, wherein the library of test peptides comprises at least one of the peptides of SEQ ID NOs: 10, 11, 12, 13, 14, 16, 17, and 18.

8. The method of claim 6, further comprising isolating the antibody that binds to the test peptide.

9. A method of detecting antibodies to peptides comprising Azetidine-2-carboxylic acid (Aze) comprising:

providing at least one synthetic test peptide comprising Aze, wherein the test peptide is a derivative of a wild-type peptide selected from a portion of a myelin basic protein (MBP) or a potassium channel Kir4.1 (Kir4.1) protein, the test peptide having at least one proline residue replaced by Aze and having an amino acid sequence selected from the group consisting of: SEQ ID NOs: 2, 3, 4, 5, 6, 7, 8, 10, 11, 12, 13, 14, 16, 17, and 18;

providing a sample from a host suspected of having multiple sclerosis, wherein the sample comprises host antibodies; and detecting binding between the test peptide and an antibody from the host sample, wherein binding indicates the presence in the host sample of an antibody to the Aze-containing peptide.

10. The method of claim 9, further comprising providing at least one control peptide having the same amino acid sequence as the test peptide, except that the control peptide has a wild-type sequence without any Aze incorporated into the peptide, and wherein the control peptide has an amino acid sequence selected from the group consisting of: SEQ ID NOs: 9 and 15;

separately contacting the host sample with the at least one test peptide the at least one control peptide;

detecting binding between the control peptide and an antibody from the host sample; and determining a difference in (a) binding between antibodies in the host sample and the test peptide and (b) binding between antibodies in the host sample and the control peptide; and upon determination of a value of (a) greater than (b), diagnosing multiple sclerosis in the host or conducting additional diagnostic tests for multiple sclerosis on the host.

11. A method of providing antibodies to peptides containing Azetidine-2-carboxylic acid (Aze) comprising:

providing a library of test peptides, the library comprising a plurality of test peptides with each test peptide comprising Aze in place of at least one proline residue, wherein the library includes at least two test peptides selected from the group of test peptides consisting of: SEQ ID NOs: 2, 3, 4, 5, 6, 7, 8, 10, 11, 12, 13, 14, 16, 17, and 18;

contacting the library of test peptides with a composition comprising one or more antibodies from a host having multiple sclerosis; and detecting binding between a test peptide from the library and an antibody from the antibody composition, wherein binding indicates the presence of an antibody to the Aze-containing peptide; and isolating the antibody that binds to the test peptide.

* * * * *